(12) United States Patent
Cohen et al.

(10) Patent No.: US 12,172,040 B2
(45) Date of Patent: Dec. 24, 2024

(54) WEARABLE, MASKLESS RESPIRATORY ISOLATION DEVICE

(71) Applicant: Emad Eskandar, Swampscott, MA (US)

(72) Inventors: James Joseph Cohen, Wenham, MA (US); Emad Eskandar, Swampscott, MA (US)

(73) Assignee: Emad Eskandar, Swampscott, MA (US)

( * ) Notice: Subject to any disclaimer, the term of this patent is extended or adjusted under 35 U.S.C. 154(b) by 653 days.

(21) Appl. No.: 17/475,729

(22) Filed: Sep. 15, 2021

(65) Prior Publication Data
US 2022/0080227 A1 Mar. 17, 2022

Related U.S. Application Data

(60) Provisional application No. 63/078,618, filed on Sep. 15, 2020.

(51) Int. Cl.
*A62B 7/10* (2006.01)
*A61L 9/20* (2006.01)
(Continued)

(52) U.S. Cl.
CPC ............. *A62B 7/10* (2013.01); *A61L 9/20* (2013.01); *A61L 9/22* (2013.01); *A62B 9/00* (2013.01);
(Continued)

(58) Field of Classification Search
CPC .......... A62B 7/10; A62B 9/00; A62B 18/006; A62B 23/02; G06T 7/20; A61B 5/087
See application file for complete search history.

(56) References Cited

U.S. PATENT DOCUMENTS 3,683,907 A * 8/1972 Cotabish ............. A62B 18/003
128/200.28
4,019,508 A 4/1977 Der Estephanian et al.
(Continued)

FOREIGN PATENT DOCUMENTS

CN 203724574 U 7/2014
CN 204337538 U 5/2015
(Continued)

OTHER PUBLICATIONS

PCT/US2021/050405, International Search Report and Written Opinion, dated Dec. 30, 2021, 13 pages.
(Continued)

*Primary Examiner* — Kathryn E Ditmer
(74) *Attorney, Agent, or Firm* — Andrus Intellectual Property Law, LLP

(57) ABSTRACT

A wearable respiratory isolation system is configured as an open collar to be worn loosely around the neck of the user, with an articulating arm positioning a mouthpiece in front of the mouth and nasal region of the user. The system provides filtered and sterilized air through a inhalation vent on the mouthpiece which creates a curtain of sterilized air in front of the users face, which protects the users face from air bourne pathogens provides sterile air for the user to inhale. Exhaled air is extracted through an exhalation vent on the mouthpiece, is decontaminated and exhausted to the rear of the user. A modified, background oriented Schlieren imaging technique is used to determine whether the user is inhaling or exhaling, and this information is used to control the flow of sterilized air and the capture of exhaled gases.

10 Claims, 10 Drawing Sheets

(51) Int. Cl.
*A61L 9/22* (2006.01)
*A62B 7/02* (2006.01)
*A62B 9/00* (2006.01)
*A62B 9/02* (2006.01)
*A62B 23/02* (2006.01)
*G06T 7/20* (2017.01)

(52) U.S. Cl.
CPC .............. *A62B 9/006* (2013.01); *A62B 9/022* (2013.01); *A62B 23/02* (2013.01); *G06T 7/20* (2013.01); *A61L 2209/14* (2013.01); *A62B 7/02* (2013.01); *G06T 2207/30201* (2013.01)

(56) References Cited

U.S. PATENT DOCUMENTS

| | | | | |
|---|---|---|---|---|
| 4,282,869 | A | * | 8/1981 | Zidulka ............ A61M 16/0633 128/200.28 |
| 5,509,414 | A | * | 4/1996 | Hok ...................... A61B 5/087 600/534 |
| 6,065,473 | A | * | 5/2000 | McCombs ............ A62B 18/003 128/200.24 |
| 6,247,470 | B1 | * | 6/2001 | Ketchedjian ...... A61M 16/0666 128/207.18 |
| 6,595,207 | B1 | * | 7/2003 | McDonald .......... A61M 16/085 128/200.24 |
| 6,805,124 | B2 | | 10/2004 | Japuntich et al. |
| 7,036,502 | B2 | * | 5/2006 | Manne ................. A62B 18/003 128/200.27 |
| 7,073,500 | B2 | * | 7/2006 | Kates ............... A61M 15/0016 128/200.14 |
| 7,118,608 | B2 | | 10/2006 | Lovell |
| 7,823,586 | B2 | | 11/2010 | Glazman |
| 9,248,248 | B2 | | 2/2016 | Virr et al. |
| 9,724,545 | B2 | | 8/2017 | Augustine et al. |
| 10,537,754 | B1 | * | 1/2020 | Vukelja ............... A62B 18/003 |
| 2008/0087282 | A1 | * | 4/2008 | Torgerson ............ A62B 18/003 128/205.29 |
| 2008/0276941 | A1 | * | 11/2008 | Doty ................. A61M 16/0666 128/207.18 |
| 2009/0205664 | A1 | * | 8/2009 | Lyon ..................... A61L 2/10 128/205.12 |
| 2010/0122705 | A1 | * | 5/2010 | Moenning, Jr. ..... A61M 16/104 128/206.24 |
| 2012/0174922 | A1 | * | 7/2012 | Virr ..................... A61M 16/106 128/206.28 |
| 2012/0199003 | A1 | * | 8/2012 | Melikov ................ G16H 50/80 454/192 |
| 2012/0279503 | A1 | * | 11/2012 | Zhou ................. A41D 13/1192 128/205.27 |
| 2015/0007810 | A1 | * | 1/2015 | Smith ................. A61M 15/00 128/200.14 |
| 2015/0174435 | A1 | * | 6/2015 | Jones ................ A62B 18/10 128/202.13 |
| 2015/0342518 | A1 | | 12/2015 | Persidsky et al. |
| 2016/0339192 | A1 | * | 11/2016 | Lee ...................... A61M 16/10 |
| 2017/0333737 | A1 | | 11/2017 | Ke et al. |
| 2017/0361133 | A1 | | 12/2017 | Yu et al. |
| 2018/0001049 | A1 | | 1/2018 | Schuller |
| 2018/0064968 | A1 | * | 3/2018 | Taslagyan ................ A61L 9/20 |
| 2018/0200544 | A1 | | 7/2018 | Liu |
| 2019/0374797 | A1 | * | 12/2019 | Jones ..................... A62B 18/10 |
| 2020/0038614 | A1 | | 2/2020 | Duff et al. |
| 2020/0139072 | A1 | | 5/2020 | Zapol et al. |
| 2022/0071748 | A1 | * | 3/2022 | Montalvo ............ A61G 13/108 |
| 2022/0080146 | A1 | * | 3/2022 | Yao ................... A61M 16/0816 |
| 2022/0105367 | A1 | * | 4/2022 | Anvari .................. A62B 18/08 |
| 2023/0301546 | A1 | * | 9/2023 | Sternberg ............ A61B 5/0836 |

FOREIGN PATENT DOCUMENTS

| | | | | | |
|---|---|---|---|---|---|
| CN | 205586379 | U | | 9/2016 | |
| CN | 105999576 | A | * | 10/2016 | |
| CN | 106621102 | A | * | 5/2017 | |
| CN | 106669056 | A | | 5/2017 | |
| CN | 106924898 | A | | 7/2017 | |
| CN | 206483003 | U | | 9/2017 | |
| CN | 105757824 | B | | 8/2018 | |
| CN | 108969858 | A | * | 12/2018 | ........ A61M 16/0051 |
| CN | 110585620 | B | | 12/2019 | |
| CN | 110624185 | A | * | 12/2019 | |
| CN | 111317897 | A | | 6/2020 | |
| CN | 111359115 | A | | 7/2020 | |
| DE | 102015122346 | A1 | * | 6/2017 | ........... F16L 13/146 |
| JP | 2017-189341 | A | | 10/2017 | |
| JP | 2019-219145 | A | | 12/2019 | |
| KR | 10-2017-0104106 | A | | 9/2017 | |
| KR | 10-1966143 | | | 4/2019 | |
| KR | 10-2020-0017064 | | | 2/2020 | |
| WO | WO-9402190 | A1 | * | 2/1994 | ........ A61M 16/0051 |
| WO | WO-2005097018 | A1 | * | 10/2005 | ........... A62B 18/003 |
| WO | WO-2007028877 | A2 | * | 3/2007 | ........... A61M 16/0683 |
| WO | 2015140776 | A1 | | 9/2015 | |
| WO | 2017103246 | A1 | | 6/2017 | |
| WO | 2018087378 | A3 | | 5/2018 | |
| WO | 2019146822 | A1 | | 8/2019 | |

OTHER PUBLICATIONS

Van Hinsburg and Rösgen, "Density measurements using near-field background-oriented Schlieren," Exp Fluids (2014) 55:1720.

* cited by examiner

WEARABLE, MASKLESS RESPIRATORY ISOLATION DEVICE

FIELD OF THE INVENTION

The invention pertains to a wearable respiratory isolation system and method that does not cover the face of the user. The wearer is supplied processed ambient air which is filtered and sterilized minimizing the potential for inhaling infectious particles. Exhaled gases are captured, filtered and decontaminated from infectious particulates prior to being exhausted.

BACKGROUND OF THE INVENTION

The recent COVID-19 pandemic has brought awareness to the vital need for protection from airborne bioactive contaminants. The use of masks has become widespread to prevent the spread of the COVID-19 virus.

There are a wide variety of masks, and some are more effective than others in filtering virions, bacteria, dust, and bioactive particulates. Even when masks are used properly, masks do not protect uncovered areas of the user's face from airborne contaminates, such as the mucous membranes of the eyes.

The use of masks also compromises the ability of people to communicate effectively. Interchange between people is enhanced by the ability to perceive facial expressions. Direct communication using voice and facial expression is important for teachers, nurses, doctors, consultants, sales personnel and for other occupations and purposes. The limitations imposed by face masks translates into numerous undesirable outcomes, including less effective teaching of school children, less effective patient care, and loss of commercial efficiency.

Traditional breathe-through masks, consisting of a porous barrier covering the wearer's nose and mouth, have changed little since their introduction for surgical procedures by William Halsted in 1890. If properly fitted and appropriately used they are effective at reducing bio-hazardous exchange under certain conditions—safely treating a limited number individuals known to be infected with a pathogenic organism (e.g. Mycobacterium Tuberculosis) or limiting the potential for nosocomial infection with drug-resistant organisms (e.g. Methicillin Resistant Staph Aureus or MRSA)

The original cloth masks have since been replaced by synthetic materials, though they still operate by deflection or entrapment of respiratory ejecta (droplets and particles). Despite their prevalence, the design of a breathe-through mask is flawed. A mask must be sufficiently porous to permit substantial gas-exchange while being impermeable to all other particles. This inherent contradiction invariably entails a trade-off between the volume of inspired and expired gas that can be transmitted in the period of one breath and the degree of filtration. Higher filtration masks, by necessity, increase the effort of breathing, requiring more effortful and longer breaths, making them unpleasant to wear. Requiring that a mask passively filters everything but nitrogen, oxygen, $CO_2$, and $H_2O$, would require too much respiratory effort and would be unusable. Hence, the highest filtration masks in use designated as "N95" filter 95% of particles yet function at the limit of tolerability for most individuals under benign conditions, and rapidly exceed the limit of tolerability for moderately effortful activities that require greater respiratory exchange.

Breathe-through masks are elementary devices that function by trapping particles in a meshwork of natural and/or synthetic material and by deflecting large air transients around the mask. Unfortunately, this design effectively increases the concentration of entrapped pathogenic viral or bacterial particles with every passing breath. After being worn for as little as 25 breaths, masks can harbor extraordinarily high bioactive toxicity. Accidental contact with such a mask by the wearer's lips, tongue, or fingers, which is not uncommon, paradoxically places a high concentration of pathogens in these locations most associated with effective viral or bacterial transmission. Appropriately, after being used, these masks are considered bio-hazardous waste and must be discarded, making them impractical except for trained healthcare-providers. Large transients, such as a sneeze or cough by the wearer, are largely unfiltered by breathe-through masks. Rather, the air is deflected and escapes around the edges of the mask.

Another major limitation of masks, as mentioned above, is the impairment of communication which relies on both auditory and visual information. Lip-reading substantially complements audition, especially when the auditory information is noisy or incomplete, while interpretation of facial expressions provides critical information about emotional tone. Masks significantly impair communication by dampening the auditory information, and all but eliminating lip-reading and interpretation of facial expression. These factors, coupled with the increased work of breathing, explaining why many people do not like wearing masks.

Alternatives to breathe-through masks are closed systems found in complete Haz-Mat suits, which are similar in design to SCUBA equipment. Such systems depend on a source of air (pressurized tanks), deploy elaborate tubing, and employ a demand regulator whose central element is a diaphragm that opens on inhalation. The demand regulator permits air to flow into the lungs through a closely applied mouthpiece and closes on exhalation directing exhaled air to a trap or filter before venting it to the environment. This design covers the face and prevents the user from eating and drinking. It also reduces the projection of speech and accompanying physiognomic expression. Such systems are highly effective at reducing exposure to the wearer, though they eliminate any hope for normal communication and are far more costly and cumbersome, rendering them unviable for consumer applications.

An object of the invention is to provide a wearable respiratory isolation device that filters and sterilizes air that is inhaled by the wearer and also decontaminates air that is exhaled by the user, and to do so leaving the user's face visually uncovered and without interfering with the ability of the user to speak clearly to another person.

SUMMARY OF THE INVENTION

The invention is a wearable respiratory isolation system which in its preferred embodiment is configured as an open collar to be worn comfortably about the neck of the user, with an articulating arm positioning an embouchure or mouthpiece in front of the mouth and nasal region of the user. The system provides filtered and sterilized air through an inhalation vent on the embouchure for the user to inhale. Exhaled gasses are extracted through an exhalation vent on the embouchure and is decontaminated and exhausted preferably to the rear of the user. The volume of filtered and sterilized inhalation air is sufficient to ensure that no unprocessed ambient gases or particulates will contaminate the user's oral or nasal normal inhalation stream. In addition, the exhalation flow is at a rate sufficient to entrain exhaled air together with ambient air, during a normal breathing process.

The wearable respiratory isolation system includes a fan, preferably a micro fan or other air moving means, to draw air through a rear intake vent and push air through a filter and through a sterilization chamber, preferably a UV-C sterilization chamber used in combination with an electrostatic precipitator. This filtered and sterilized air then flows into a sterilized air inhalation reservoir where it is stored. A valve traps the filtered and sterilized air in the inhalation reservoir and the tube connecting to the embouchure. The delivery of the inhalation gas is controlled and modulated by means of a modulation valve situated within the inhalation vent in the embouchure. The inhalation vent is adapted to be located near the user's face and is configured so that a cloud of filtered and sterilized air is presented in front of the nose and the mouth of the user when the user inhales. In the exemplary embodiment of the invention, a relatively low level of filtered and sterilized inhalation air is provided when the wearer is not exhaling or inhaling. The low flow of processed inhalation gas helps to protect the face from contamination and ensures that the user will have sterilized gases to breathe at the onset of inhalation. When the onset of inhalation is detected, the modulation valve is controlled so that an appropriate amount of additional inhalation gas is provided for the wearer to inhale.

The invention uses a modified Schlieren imaging technique, referred to herein as Synthetic Adaptive Schlieren (SAS), based on advances in near-field background-oriented Schlieren (BOS) technology, to sense in real time whether the user is inhaling, exhaling or not inhaling or exhaling above a certain threshold. The exemplary embodiment of the invention employs a modified version of the technique described in the article entitled "Density measurements using near-field background-oriented Schlieren," by van Hinsburg and Rösgen, Exp Fluids (2014) 55:1720. In the preferred embodiment, a pair of imagers (e.g. high speed camera) and illuminators (e.g., a narrow band-UVC LED, 222 nm) on the embouchure and software are used to detect the density and/or the density gradient of air in the region below the user's nostrils and ahead of the user's mouth. This region is referred to as the vestibule region. Schlieren imaging is a method used to visualize density variations in transparent media which are not normally visible to the human eye. Optical inhomogeneities cause localized differences in the optical path, which in turn cause light deviations that produce localized brightening, darkening or even color changes.

The exemplary embodiment of the invention utilizes the bioorganic surface of the wearer's face to serve as the source of stochastic patterned background. The areas are illuminated with a low level of near-UV light which is not perceptible to the human eye but is easily resolved by the ipsilateral and contralateral imagers on the embouchure. The physiognomic surface features most appropriate for this algorithm are the spaces between the facial pores situated in the areas above the alares and below the periorbita, i.e., the maxillary region. This area is rich in detail and does not shift rapidly. The patterns emergent from the areas between the pores are used in the SAS or modified BOS imaging technique. The imaging path for the ipsilateral imager is direct to the maxillary area on the ipsilateral side of the user's face, while the imaging path for the contralateral imager passes through the vestibular region where the user is inhaling and exhaling. Sequential imaging data is analyzed by software in real time to determine whether the image shows an inhaling air flow, an exhaling air flow, and if so the relative rate of gas flow.

The system cycles under normal respiration conditions to provide a relatively low flow of filtered and sterilized gas before the system senses the onset of inhalation. The exhalation modulation valve is normally closed at this point in the process. The flow creates a cloud or curtain of filtered and sterilized gases in the region of the user's face so that the user will inhale filtered and sterilized air when they being to inhale. The cloud or curtain of filtered and sterilized air also protects the user's eyes and face. When the SAS sensors and software detects that inhalation has begun, the control system opens the inhalation modulation valve to release an appropriate amount of additional gas to ensure that enough filtered and sterilized air is available to be inhaled. For example, a larger amount of filtered and sterilized inhalation air is provided when the user is exercising and breathing harder than when at rest. The exhalation modulation valve remains closed when the inhalation modulation valve is open. When the user has completed inhaling, a low level of filtered and sterilized air is supplied until it is detected that the user is beginning to exhale. At that point in the cycle, the inhalation modulation valve is closed and the exhalation modulation valve is opened in an appropriate amount in response to the exhalation flow detected by the SAS sensor. The flow rate through the exhalation vent will normally be three to four times the maximum flow rate of the inhalation vent. The exhalation flow rate is expected to be significant enough to draw in all exhalation gasses during normal respiration, as well as ambient air. In the event of a cough, sneeze or other similar event, the system can operate in a collection mode in which the exhalation draw is maximized for the current cycle and for several subsequent cycles. It may also be desirable to implement techniques to redirect the direction of a cough or sneeze plume, prior to operating in collection mode. For example, it may be advantageous to provide a burst of inhalation or oxygen through the inhalation vent in the embouchure to counteract the flow of a cough or sneeze.

It is also possible to use a diaphragmatic respiratory sensor to determine predictively when the user will inhale or exhale. A diaphragmatic respiratory sensor can be used to supplement the optical SAS datum by providing predictive information as to the timing of inhalation and exhalation as well as the volume of the inhalation or exhalation. A diaphragmatic respiratory sensor can be helpful for example in predicting respiratory eruptions such as yawning, sneezing, coughing and eructations. In an alternative embodiment of the invention, a diaphragmatic respiratory sensor can be used in place of the optical Schlieren imaging system.

As mentioned, a first micro fan(s) moves the air through an inhalation path, in which it is filtered and sterilized. The exemplary system uses a replaceable MERV 12 rated filter (or greater) on the inlet side to trap 1.0-3.0 μm particles with an efficiency of >99%. Additionally, a pre-filter reusable mesh collects particles greater than 10 microns. The preferred sterilizer comprises an inline LED UVC germicidal chamber with a particulate ionization precipitator. The particulate ionization precipitator includes a dielectric array and precipitation plates. The filtered and sterilized air is continuously pumped into the sterilized inhalation air reservoir. An inhalation modulation valve is located downstream of the sterilized inhalation reservoir. The controller opens the valve to release filtered and sterilized air from the sterilized inhalation reservoir through the inhalation vent on the embouchure in front of the user's face.

A second micro fan(s) draws exhalation gas and ambient air into the exhalation vent which is co-located in the embouchure similarly situated near the user's oral and nasal vestibular area. The second fan draws air into the exhalation path at a sufficient rate to capture exhalation gases by the user in combination with ambient air in order that essentially all expired or exhaled gas is entrained within the air flow that is drawn into the exhalation vent and through the exhalation air path. Another modulation valve is located in the exhalation path between the exhalation vent and an exhalation reservoir. The second fan is downstream of the exhalation reservoir and creates a negative pressure or slight vacuum that draws the expired gas into the exhalation vent, through the valve and into the exhalation reservoir.

DETAILED DESCRIPTION

The figures illustrate a wearable respiratory isolation system 1 constructed in accordance with an exemplary embodiment of the invention. The wearable respiratory isolation system 1 provides a stream of filtered, sterilized air for inhalation by the wearer, thereby protecting the user from harmful pathogens. The wearable respiratory isolation system 1 also captures exhalation, and sterilizes it at least partially, before releasing it into the environment, thereby protecting others. The system 1 requires no increase in the work of breathing and enables free and unimpeded communication because the user's face is left open to plain view and because the fans, motors and air flow associated with the system 1 are very quiet.

Both the inhalation process and the exhalation process are subject to aseptic control (via a UV-C germicidal chamber). This provides the wearer with the certainty that they are, as to respiration, antiseptically isolated from the ambient environment. Further, the system 1 ensures that the wearer will not pollute the ambient environment with respiratory production of bioactive material under normal respiration conditions.

Figure 1:
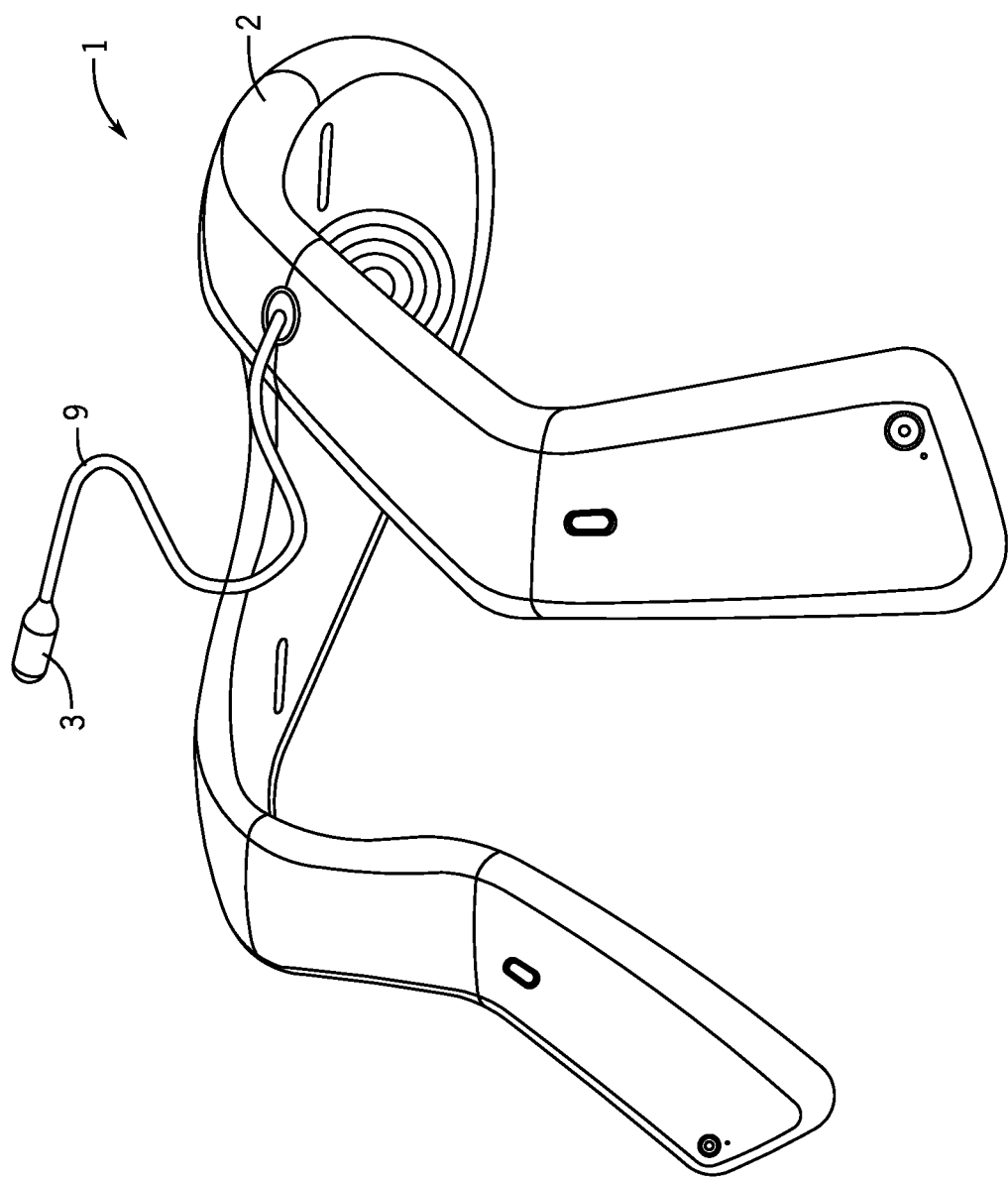
FIG. 1 is a front perspective view of a wearable respiratory isolation system constructed in accordance with an exemplary embodiment of the invention.
Figure 2A:
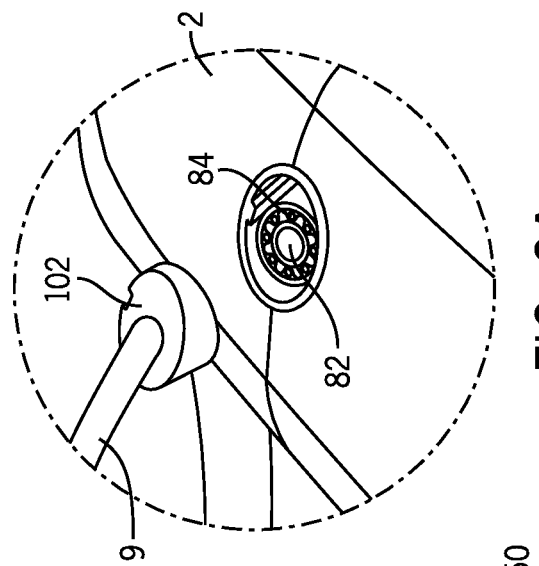
FIG. 2A is a detailed view showing the attachment of an articulated arm to a collar of the system shown in FIGS. 1 and 2.
Figure 2:
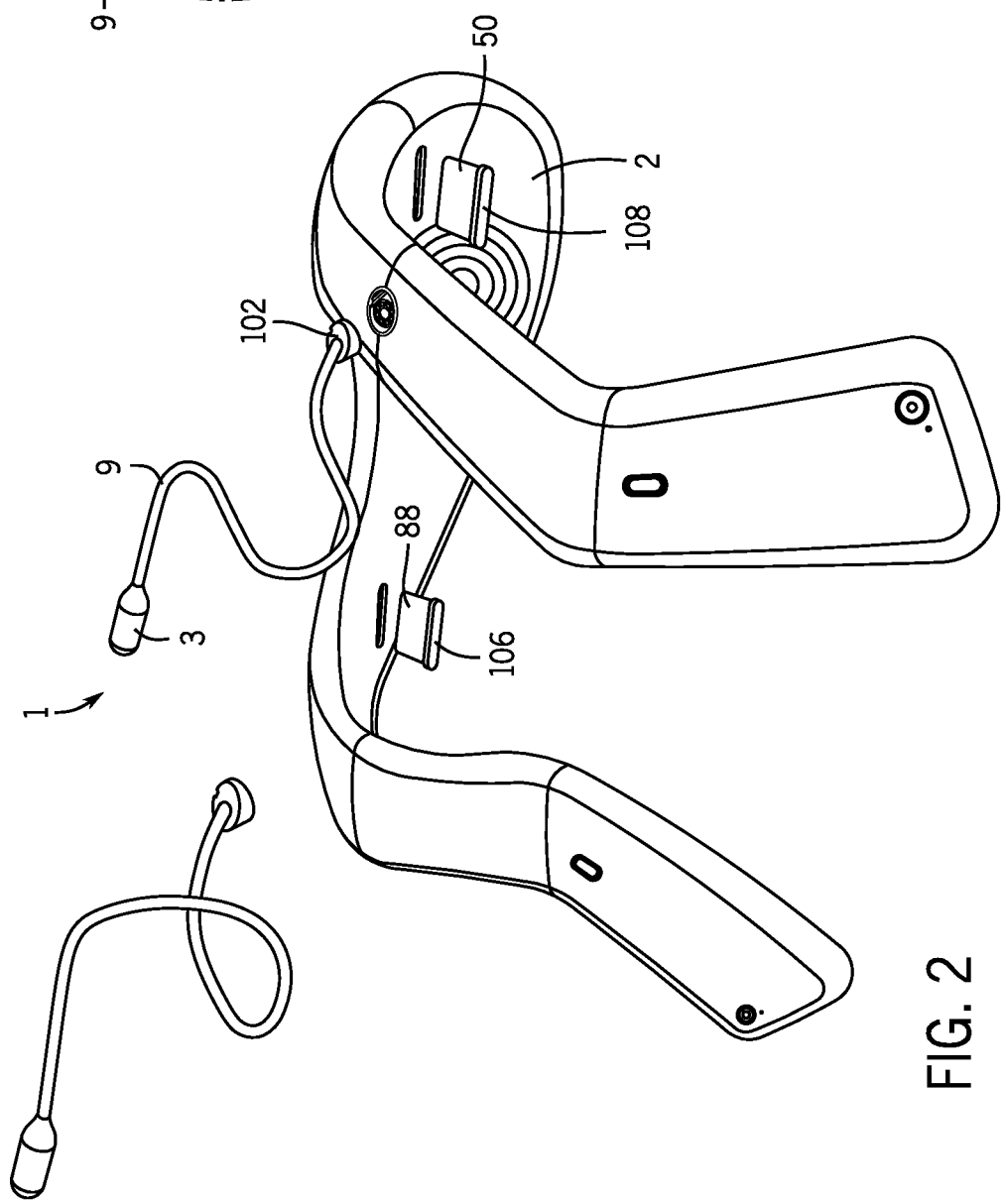
FIG. 2 is a front perspective view of the wearable respiratory isolation system shown in FIG. 1 with parts detached.
Figure 3A:
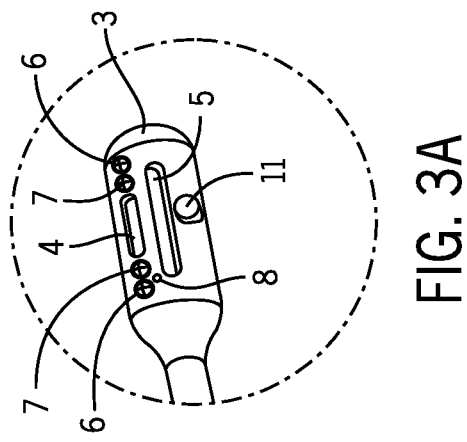
FIG. 3A is a detailed view showing a detailed view of the components on the mouthpiece or embouchure.
Figure 3:
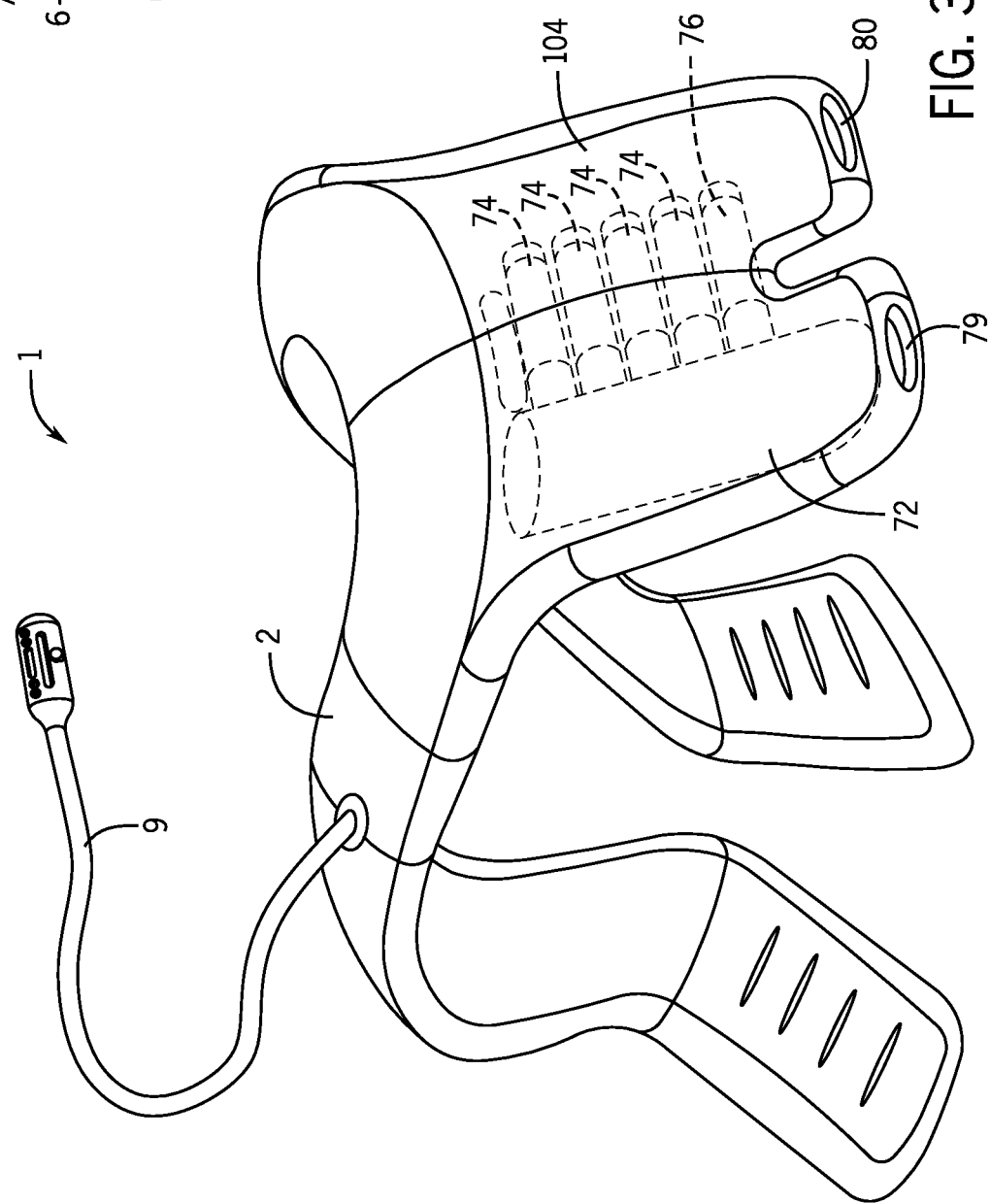
FIG. 3 is a rear perspective view of the wearable respiratory isolation system shown in FIGS. 1 and 2.

Referring first to FIGS. 1 and 2, the system 1 comprises an open collar 2 in which the other components of the system are carried or on which the other components are mounted. The collar 2 sits around the neck of the user and has an open front. An articulating arm at 9 is attached to the collar 2. A mouthpiece or embouchure 3 is attached to the end of the articulating arm 9. Referring to FIG. 3, the mouthpiece 3 includes an inhalation vent 4, an exhalation vent 5, a pair of coextensive Schlieren illuminators/imagers 6, 7, an ultrasonic transducer 11 and a microphone 8. The articulating arm 9 includes an umbilical to connect air flow, DC power, data signals and control signals between the main collar 2 and the mouthpiece 3. Modulation valves 16, 17 (FIG. 5) are also located within the mouthpiece 3 and control the rate of air flow through the inhalation vent 4 and into exhalation vent 5. The articulated arm 9 is removable from the collar 2 in the exemplary embodiment.

The wearable respiratory isolation system 1 provides a filtered and sterilized air-inhalation at sufficient volume to satisfy a complete inhaling breath by the user, and similarly captures (and then filters and decontaminates) a sufficient volume of air in front of the user's face to account for all the exhalation as well as some ambient air under normal respiratory conditions. The system 1 flow rates in the exemplary embodiment are chosen to satisfy these requirements at normal resting ventilation and to higher levels as needed up to and including the respiratory exchange associated with moderate exercise.

Figure 5:
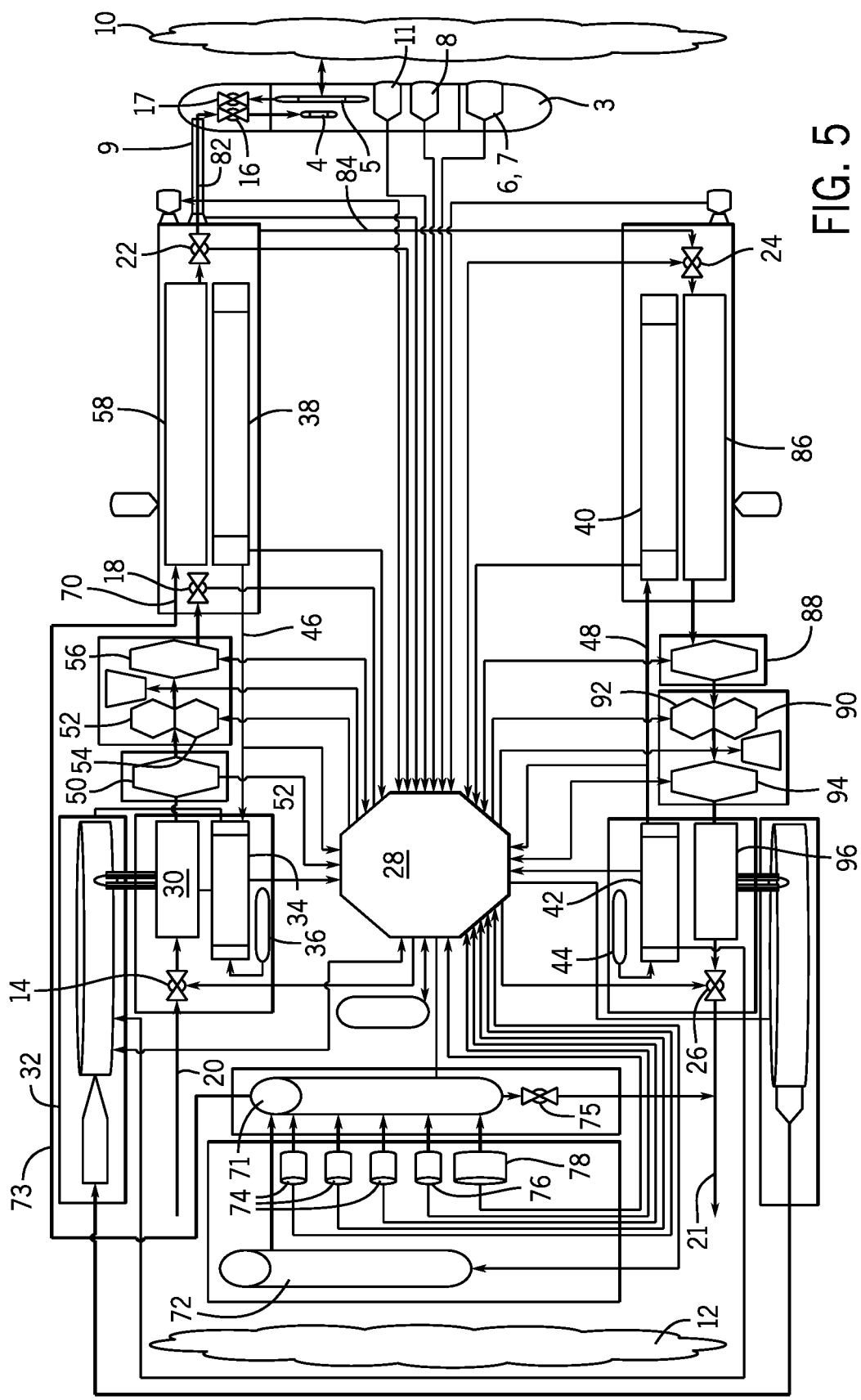
FIG. 5 is a flow diagram showing the overall operation of the wearable respiratory isolation system shown in FIGS. 1 through 4.

FIG. 5 is a flow chart illustrating operation of the wearable respiratory isolation system 1. The inhalation airpath is shown along the top of the chart in FIG. 5, and the exhalation path is shown along the bottom of FIG. 5. The right-hand side of FIG. 5 shows the mouthpiece 3 which is located in front of the user's face when the system 1 is in use. A cloud or curtain of filtered and sterilized air 10 is depicted for illustrative purposes. The left-hand side of FIG. 5 shows ambient air 12 to the rear of the user. Many of the components in the system receive DC power and are controlled by control electronics 28 that are contained within the collar 2. The control electronics 28 contain software to implement many of the functions of the system 1.

In general, the system 1 intakes ambient air 12 from the rear of the user, filters and sterilizes the air, and supplies the filtered sterilized air from the inhalation vent 4 on the mouthpiece 3 in order to form the curtain or cloud 10 of sterilized gas in front of the user's face for the user to inhale. The cloud or curtain 10 of sterilized gas also protects the user from environmental pathogens as mentioned earlier. When the user exhales, the exhaled breath along with some ambient air is drawn into the exhalation vent 5 on the mouthpiece 3 and is pulled through the exhaust path, filtered and decontaminated prior to being exhausted to the rear 12 of the user. The term decontaminated is used to emphasize that sterilization of the exhalation gases in the exhalation path may not be complete. Flow rates through the exhalation path are normally significantly higher than the flow rates through the inhalation path, so the germicidal chamber may not have sufficient capacity to fully sterilize the exhaust gases. Nevertheless, the sterilization process in the exhalation path is effective in reducing the numbers of active pathogens in the exhaust, and the exhaust is to the rear 12 of the user thereby isolating the person to whom the user is speaking or interacting with. While it may not be necessary to size the components in the exhalation path to ensure full sterilization, it can be done within the scope of the invention.

Figure 4:
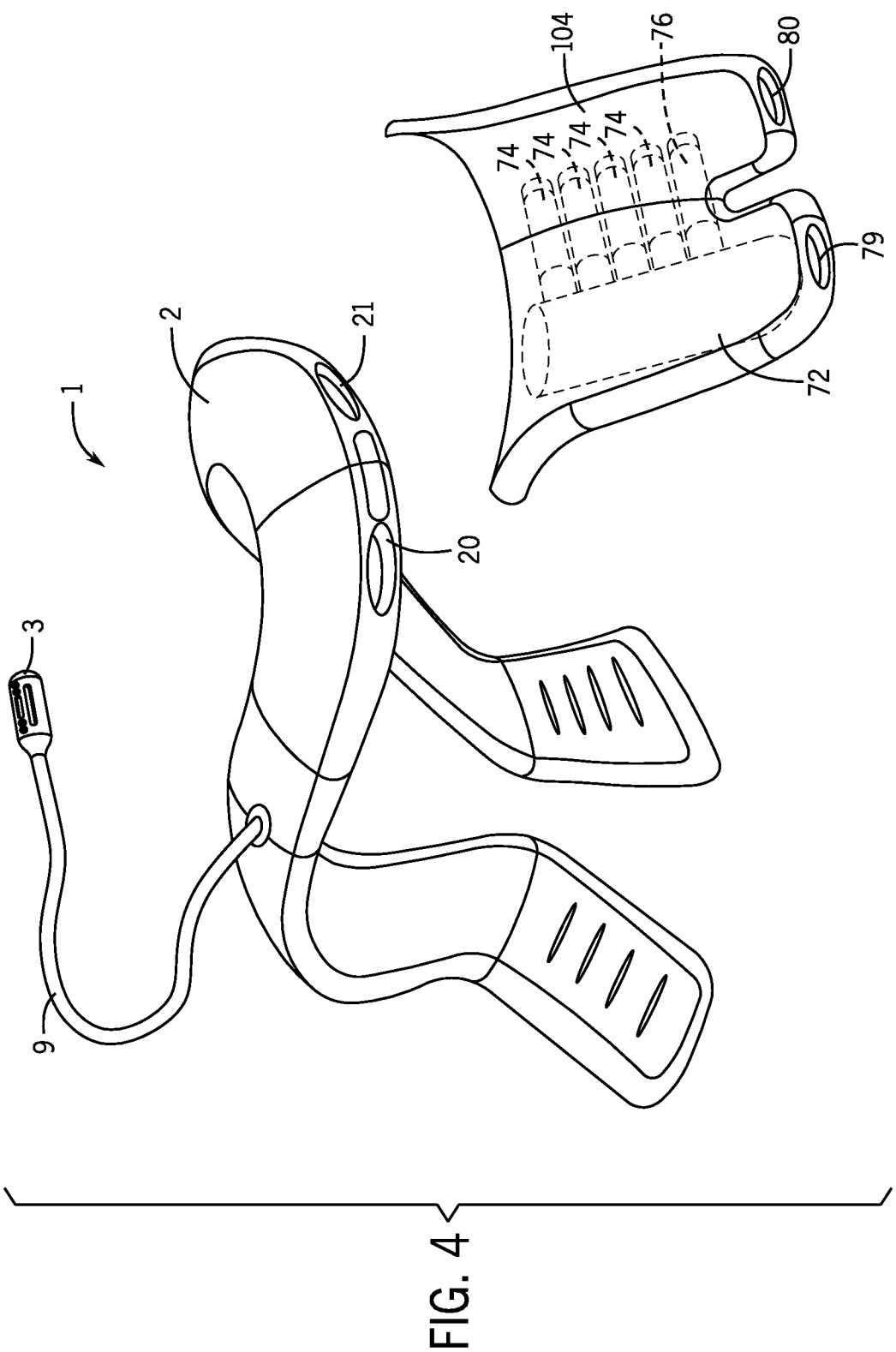
FIG. 4 is a rear perspective view similar to that shown in FIG. 3 with an augmentation pack attached to the rear of the collar.

Referring to the left-hand side of FIG. 5, ambient air 12 is drawn into the inhalation path through the ambient air inlet 20 located on the rear side of the collar 2, see FIG. 4. An isolation valve 14 is provided at the inlet 20. Isolation valve 14 is a hemispheric valve or ball valve controlled electronically by the controller in the exemplary embodiment. Other types of electronically controlled isolation valves can be used without departing from the scope of the invention. This isolation valve 14 as the other isolation valves (18, 22, 24, 26) in the system 1 are normally closed valves but are opened by the control electronics 28 when the system 1 is in operation. Downstream of the isolation valve 14, the inhalation gas flows through an inhalation reservoir 30. In the exemplary embodiment of the invention, the inhalation gas in the ambient intake reservoir 30 can be heated for example using a heat pump 32 or a resistive heater if it is desirable to heat the gases supplied through the inhalation vent 4 in the mouthpiece 3. In the exemplary embodiment, the isolation valve 14 and the ambient intake reservoir 30 are part of a replaceable, modular unit also containing a rechargeable battery 34 an induction charging pad 36. It is desired that the modular unit be swappable or replaceable so that one can replace the battery 30 easily if necessary, or for convenience. In the exemplary embodiment, the replaceable battery 30 is rechargeable lithium polymer battery, 4.2 Volt, 1500 mAh. The system 1 includes other batteries 38, 40, 42 as well. Another lithium polymer 4.2 Volt battery but with a higher output current, namely 2500 mAh is fed power from a power bus 46 from the swappable, rechargeable battery 34. This way, both batteries 34, 38 on the inhalation side of the system can be charged by the induction charging pad 36 on the inhalation side of the system 1. As discussed below, there is a similar battery power set up on the exhalation side of the system 1.

Downstream of the inhalation intake reservoir 30, the inhalation air flows through a MERV filter 50. The exemplary system 1 uses a replaceable MERV 12 rated filter (or greater) on the inlet side of the micro fan(s) to trap 1.0-3.0 particles with an efficiency of >99%. Additionally, a pre-filter reusable mesh over the intake 20 collects particles greater than 10 μm. Air passes through the MERV filter 50 and is then drawn through dual, parallel micro fans 52, 54. Dual micro fans are used in order to increase the air flow volume through the inhalation side. Axial micro fans made by SEPA model MF 15A-05 (DC brushless, DC 5V, 80 mA operating current) are used in the exemplary embodiment, although other micro fans may be suitable. The exemplary micro fans have a flow rate of 10.0 to 0.6 liters/minute. In the exemplary embodiment, a printed circuit board with a synchronizer is used to ensure that the parallel fans 52, 54 operate synchronously. Depending on the size and power of the fans 52, 54, as well as several other factors, it may be desirable to use fans in series or use a combination of fans in series and in parallel, to ensure that the system 1 has a sufficient flow of sterilized air. As described, dual axial micro fans are the means for moving air and gasses through the inhalation path in the exemplary embodiment and, as discussed below through the exhalation path. The use of blowers, or compressors with rotary or reciprocating pumps, while not preferred, are alternative means of moving air and gasses through the inhalation path and the exhalation path.

After passing through the filter 50 and the dual fans 52, 54, the inhalation air passes through a sterilizer/precipitator germicidal chamber 56 that ionizes and collects remaining bioactive material (virions, bacteria, and large molecular weight aerosols). The sterilized respiratory inhalation gas (sterilized air) is then passed to an inhalation reservoir 58 in preparation for delivery through the mouthpiece 3.

Figure 6:
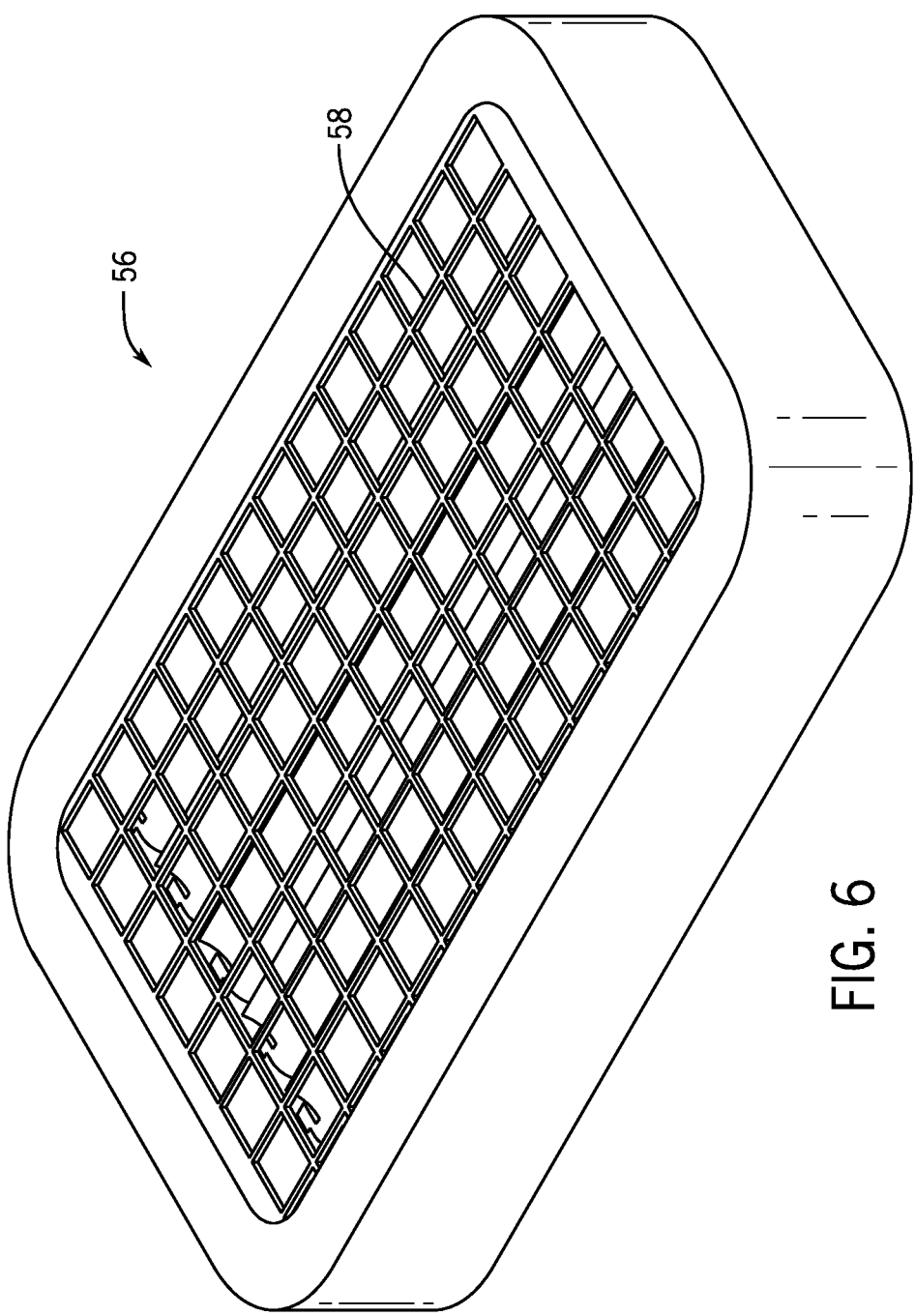
FIG. 6 is an isometric view of an UVC sterilizer and precipitator.
Figure 7:
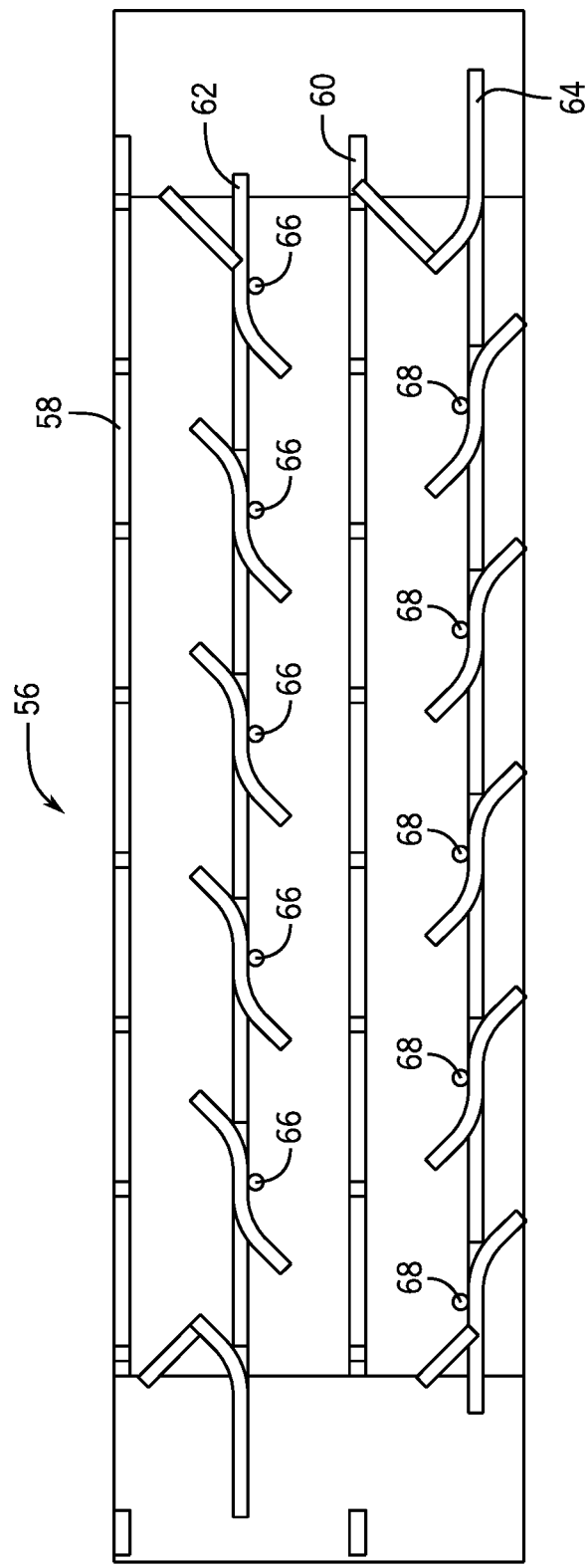
FIG. 7 is a cross section of the UVC sterilizer and precipitator.

The sterilizer/precipitator chamber 56 is shown in FIGS. 6 and 7. FIG. 6 is an isometric view showing the inlet side of the chamber 56 through which the air flows into the chamber 56. FIG. 7 is a cross-sectional view of the chamber 56. The sterilizer/precipitator chamber 56 has two grates 58 and 60 and two sets of vanes 62, 64. A driver (not shown) provides voltage to the vanes 62, 64 and the grates 58, 60, which are electrodes. The potential difference between the electrodes is relatively high, for example 1.5 kV across a distance of about 1 millimeter. The grates 58, 60 and the vanes 62, 64 are perpendicular to the general direction of the airflow and provide a relatively constant potential gradient in the airflow path. The vanes 62, 64 redirect the airflow so that it becomes more turbulent as it passes through the chamber 56 in which the electrodes are located. Although not shown in FIGS. 6 and 7, the sterilizer includes multiple UV-C LED emitters, preferably narrowband LEDs emitting UV radiation at 222 nanometers. The UV-C LED emitters are coupled to light pipes 66, 68, e.g. UV-grade, fused silica fibre with low cladding to facilitate for effective scattering. The series of light pipes run parallel to the grate 60 between the sets of vanes 62, 64 with some upstream 66 of the grate 60 and some 68 downstream of the grate 60. The light pipes 66, 68 disperse UV-C radiation towards particles that have been attracted to the electrodes or are otherwise within the path of the UV-C radiation. The vanes 62, 64 desirably have a reflective surface to help redirect the UV-C radiation efficiently.

Positively charged ions are precipitated onto the negatively charged electrodes, which are the sets of vanes 62, 64 in the preferred embodiment, although it is contemplated that the grates 58, 60 can be negatively charged in other embodiments. While some virions may ionize when passing the electrodes, UV-C radiation is the primary mode of ionizing virions in the air flow in the chamber 56. Ionization of the virions by the UV-C radiation results in positively charged particles that are attracted to the negatively charged surfaces. Upon contact, positively charged, ionized virions adhere to the negatively charged surfaces due to the electrostatic attraction, negatively charged ions are attracted to positively charged surfaces, and the ionized virions are continuously radiated with UV-C radiation. Eventually, the virions absorb sufficient energy to break intramolecular bonds on the surface of the virion capsule or disrupt molecular RNA, and the precipitates are no longer capable of any pathogenic activity. Alternatively, bioactive particles tend to be polarized which causes them to be reactive to living cells. Due to this polarization, the bioactive particles will tend to stick to either the anode or cathode depending on the level of polarization due to electrostatic forces. Upon adhering to the electrode, the bioactive particles will then be continuously irradiated with UV-C, thus rendering the particles inactive.

The internal metal components of the sterilizer/precipitator could be coated with an inert substance such as gold plating or SilcoNert 2000 to maximize the amount of collected particles over time and ease of cleaning.

In an alternate embodiment, the charge of the anodes and cathodes could be switched to allow for more selective precipitation of bioactive molecules. This switching may occur for example at a frequency of 10 to 20 Hz, although frequencies in the range of 0.1 to 1000 Hz may be suitable.

Accordingly, within the sterilizer/precipitator germicidal chamber 56, materials not collected by the MERV filter 50, are ionized and attracted to the anode grate 60 via electrostatic forces. The anode grate 60 is under continuous UV-C radiation which not only ionizes large molecules but decomposes the bioactive materials (Manuela Buonanno, 2020), thereby sterilizing the air passing through the chamber 56. This assembly is not intended to change the basic chemical makeup of the air, just remove bioactive components and large molecular weight aerosols.

Alternatively, sterilization may be performed by the use of other forms of radiation such as x-rays or gamma rays. Sterilization on the exhalation side can also be performed by chemical means through the use of aerosol liquids and solids (such as bleach and alcohols) or gasses such as ozone or toxic chemicals. Alternatively, sterilization can be performed by temporarily raising the temperature of the air and gasses or the flow path. As another alternative, sterilization can be performed by forcing the flow through a fine filter so that only the desired small molecular gasses of nitrogen, oxygen, and carbon dioxide pass. These embodiments are less desirable than the exemplary one described herein.

Referring again to FIG. 5, on the inhalation side, the filtered and sterilized air flows from the sterilizer/precipitator chamber 56 into the sterilized air inhalation reservoir 58. An isolation valve 18 is located upstream of the sterilized air inhalation reservoir 58 and another isolation valve 22 is located downstream of the sterilized air inhalation reservoir 58. As discussed previously, these isolation valves 18, 22 can be hemispheric valves or ball valves and are normally closed. The control electronics opens the isolation valves 18, 22 during normal operation. When the system is turned off, the isolation valves return to their normally closed position. As depicted in FIG. 5, it is desirable that the sterilized air inhalation reservoir 58 and the rechargeable battery 38, along with the isolation valves 18, 22 be part of a module that can be separately removed and replaced during maintenance of the system 1.

The pressure in the sterilized air inhalation reservoir 58 will normally be at atmospheric pressure or slightly above. FIG. 5 indicates that there is optionally an aerosol manifold 71 with one or more ports 70 to receive amendments to the sterilized air. A conduit 73 connects the aerosol manifold 71 to the volume contained by the sterilized air inhalation reservoir 58. For example, it is possible to attach an oxygen canister 72 containing pressurized oxygen to the manifold 71, in order to feed pressurized oxygen into the reservoir 58 in dosed amounts to increase the amount of oxygen in the air inhalation stream. It may be desirable to have an oxygen sensor in the reservoir or downstream to sense the level of oxygen in the inhalation air. Even though FIG. 5 does not show a valve controlling the flow of oxygen in conduit 73 into the sterilized air inhalation reservoir 58, the exemplary system 1 has such a valve. Similarly, other amendments to the inhalation air besides oxygen can be added using aerosol cartridges 76 or nano cartridges 74, which are connected to the aerosol manifold 71. The pressurized oxygen 72 can be used to mix with the amendments 74, 76 and supply the amendments through the conduit 73 to the inhalation reservoir 58. These amendments include medications, therapeutics, aesthetics, and nano therapeutics.

FIG. 5 also shows a sterilization cartridge 78 that contains a sterilization agent and is used to sterilize the air inhalation reservoir 58 from time to time when the system 1 is not in use. To do this, the system 1 operates in a sterilization mode in which the isolation valve 18 upstream of the sterilized air inhalation reservoir 58 is closed. The sterilizing agent is injected from the canister 78 into the manifold 71 and subsequently into the air inhalation reservoir 58. Then, the isolation valve 22 downstream of the reservoir 58 is closed allowing the sterilization agent to disinfect the reservoir 58. The downstream isolation valve 22 is then opened and a rinsing fluid, e.g., filtered and sterilized air or pressurized oxygen, is pushed through the sterilized air inhalation reservoir 58 and the downstream isolation valve 22. It is contemplated that the articulated arm 9 and mouthpiece 3 can be attached during the sterilization mode if it is desired to sterilize the inhalation air flow path (conduit in articulating arm 9, valve 16 and vent 4).

An isolation valve 75 is provided between the aerosol manifold 73 and the waste outlet. This isolation valve 75 can be opened to empty the contents of the aerosol manifold 71 in to the exhaust stream prior to exiting the system.

Still referring to FIG. 5, in normal operation, the sterilized air stream, with or without amendment, flows into the articulated arm 9, and through the modulation valve 16 and the air inhalation vent 4 on the mouthpiece 3. The air inhalation modulation valve 16 controls the flow of the filtered and sterilized air stream through the air inhalation vent 4 As shown in FIG. 5, the flow of sterilized air through the air inhalation vent 4 builds a cloud or curtain 10 of sterilized air in the space in front of the user's face and, in particular, in front of the users mouth and nostrils. It is desired that the modulation valve be located on the embouchure 3 so that there is no latency or very little latency in controlled air flow rate after the valve is modulated, opened or closed. As mentioned previously, the inhalation modulation valve 16 is controlled to release at least a low level of air flow, at all times, during a normal respiration cycle when the user is not exhaling. However, when it is detected that the user is exhaling, the inhalation modulation valve is closed and remains closed until it is determined that the user is no longer exhaling. Once it is determined that the user is no longer exhaling, the inhalation modulation valve is opened to release a low level of sterilized airflow again, thereby building the curtain or cloud of sterilized air 10 in front of the user's face. The inhalation modulation valve 16 is open further when the user beings to inhale.

An exhalation modulation valve 17 and an exhalation vent 5 are also on the multipiece 3. It is desirable that the exhalation modulation valve be on the mouthpiece 3 in order to minimize exhalation air flow latency compared to the electronic control of the exhalation modulation valve. In normal operation during a normal respiration cycle, the exhalation modulation valve 17 is closed when the inhalation modulation valve 16 is open. In other words, the exhalation modulation valve is during a normal respiration cycle except when the system detects that the user is exhaling. The exhalation that is drawn in through the exhalation vent 5 passes through a conduit in the articulating arm 9 and a flow channel 84 in the collar 2 that leads to the exhalation reservoir 86. The exhalation gasses flow through a MERV filter 88 before flowing to dual fans 90, 92. Downstream of the fans 90, 92, the exhalation gasses pass through a sterilizer/precipitator chamber 94 prior to being released into an exhaust outlet reservoir 96 and to the ambient environment 12. In the exemplary embodiment, the MERV filter 88 in the exhalation path is the same as the MERV filter 50 in the inhalation path. In addition, the dual fans 90, 92 and sterilizer precipitator chamber 94 are a part of a replaceable module that is the same as the module used on the inhalation side. As mentioned, the flow rates through the exhalation path will be normally higher than the flow rates thru the sterilizer precipitator germicide chamber on the inhalation side, which means that exhaust air may not be completely sterilized. Nevertheless, the exhaust air is decontaminated or sterilized, in part, to reduce the pathogen activity in the exhaust flow. In other embodiments, it is possible to equip the exhalation path with the capability of sterilizing increased volumes of airflow. The exhaust flow is exhausted to the rear of the user, see port 21 on the collar 2 in FIG. 4 and port 80 on the extension in FIG. 3, thereby substantially reducing the risk of contamination to a person speaking to the wearer, even if the exhaust air is not completely sterile.

Still referring to FIG. 5, it is desirable that the components on the exhalation path be the same or similar to the components on the inhalation path in order to simplify assembly and manufacture. The exhalation side also includes an induction charging pad 44 and a rechargeable battery 42 (e.g. lithium polymer) surrounding the exhaust outlet reservoir 96. The exhaust outlet reservoir 96 can be used, as shown in FIG. 5, to draw heat from the exhalation path air in the event that a heterodyne heat pump is used. Even if exhaust outlet reservoir 96 is not used to draw heat from the exhalation path, it may be practical to use the same module containing an induction charger, a rechargeable lithium-polymer battery, a reservoir and an isolation valve for the exhalation path side as is used on the inhalation side. The exhalation side also includes another battery 40 surrounding the exhalation reservoir 86 and a power bus 48 to transfer power to the rechargeable battery 40 surrounding the exhalation reservoir 86, similar to the inhalation side. It is noted that the module for the exhalation reservoir 86 and its battery 40 as shown in FIG. 5 includes an isolation valve 24 upstream of the reservoir 86 but does not include a valve downstream of the reservoir 86. It is contemplated, however, that the same module can be used for the sterilized air inhalation reservoir 38 and the exhalation reservoir 86, in which case an isolation valve would be located downstream of the exhalation reservoir in FIG. 5.

FIG. 5 shows the control electronics 28 receiving signals and controlling the operation of the various components of the system. In addition, the controller can receive input from various environmental or physiologic sensors if desirable. It is also contemplated that the system will operate on voice command from the user. In this regard, the microphone 8 on the mouthpiece 3 is used to accept voice commands from the user, e.g., first using a code word to activate the voice command mode. The system also includes speakers which are located on the collar 2 and enable the controller to provide audible signals or notices to the user, such as low battery etc. The control electronics also includes software for controlling the position of the mouthpiece 3 as well as the rate at which the fans 52, 54, 90, 92 operate and the operation of the modulation valves 16, 17 for the sterilized air inhalation vent 4 and the exhalation vent 5 on the mouthpiece 3.

Figure 8:
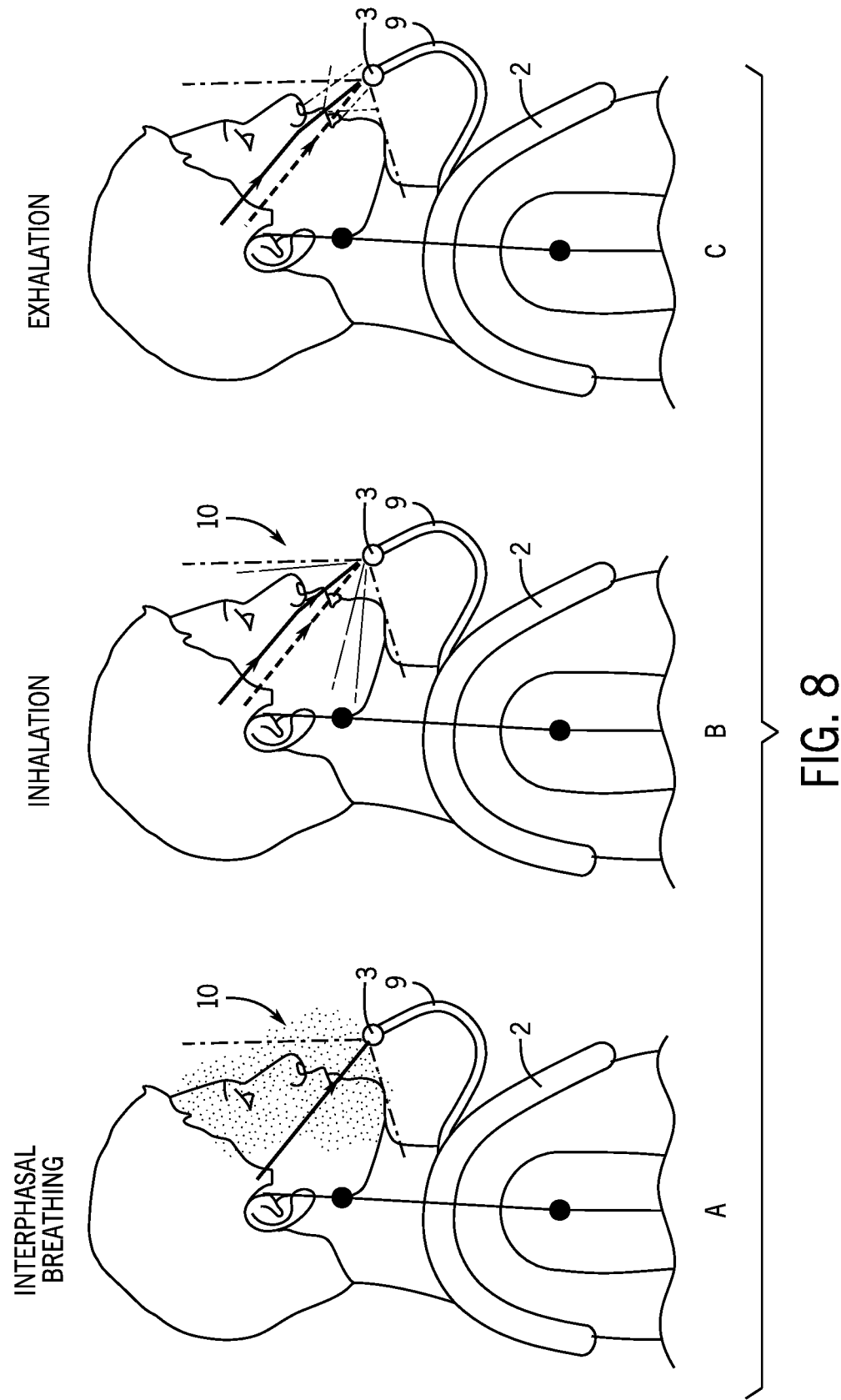
FIGS. 8A through 8C schematically illustrate operation of a wearable respiratory isolation system constructed in accordance with the exemplary embodiment of the invention.

Referring now to FIGS. 8A through 8C, the mouthpiece 3 is desirably located in a fixed location with respect to the user's face in front of the user's mouth and nostril, for example as shown in FIGS. 8A through 8C. The articulating arm 9 moves the mouthpiece 3 as described in more detail below in order to maintain the relative position and orientation of the mouthpiece 3 to the user's face. Under normal respiratory conditions, the system 1 includes three phases of operation: inter-breath as shown in FIG. 8A, inhalation as shown in FIG. 8B, and exhalation as shown in FIG. 8C. During the inter-breath phase, as discussed, a low level of sterilized air is provided through the inhalation vent 4 in the mouthpiece 3 to build a cloud or curtain of sterilized air 10 in front of the user's face. The Schlieren sensor takes images of a stable portion of the user's face at all times, and during an inter-breath phase determines if and when the user begins to inhale or exhale. Signals from the imager 6, 7 on the mouthpiece 3 are also used to track the position of the mouthpiece 3 with respect to the user's face. The sampling rate of the camera 6, 7 or imager 6, 7 is sufficiently fast so that the mouthpiece 3 can adequately track the movement of the user's face and also quickly detect the onset of inhalation or exhalation using a modified, background oriented Schlieren (BOS) algorithm. This modified version of (BOS) is referred to in this document as Synthetic Adaptive Schlieren (SAS). The SAS technique detects the refraction of incident light rays to determine whether there is fluid movement in the pathway of the light. In the inter-breath phase is shown in FIG. 8A, there is no refracted light detected, or a low level of refracted light below a threshold, which indicates that there is no or little fluid movement. FIG. 8B shows the situation in which the user has begun to inhale. In this case, the refraction of light is detected to indicate that there is fluid movement and the software calculates that is an inhaling event. FIG. 8B shows that under these conditions sterilized air is supplied at a higher level to provide a greater density of sterilized air in the space 10 in front of the user's face and, in particular, in the space in front of the user's nostrils and mouth. When the sensor/software detects that the user is no longer inhaling, the system reverts to the inter-breath phase, FIG. 8A, until the sensor and the software detect that the user is exhaling (or inhaling again). FIG. 8C shows the system operating while the user is exhaling. When the software detects that the refraction pattern corresponds to an exhale event, the inhalation air modulation valve 16 is closed and the exhalation modulation valve 17 for the exhalation vent is opened. The vacuum created by the fans 90, 92 in the exhaust path draws exhaled gases into the exhalation vent 5 as well as other ambient air.

To summarize, the mouthpiece 3 tracks but does not touch the wearer's nose and mouth. The imaging sensors 7 on the mouthpiece 3 along with imaging software determines the speed and direction of respiratory airflow. Airflow through the air inhalation 4 and exhalation 5 vents are synchronously modulated to accommodate respiratory activity such as breathing, yawning and coughing.

The system functions by capturing ambient air through an intake port 20 at the back of the collar 2, filtering and sterilizing the air to establish and continuously replenish the reservoir 38 with sterilized air that is delivered in synchrony with inhalation by the mouthpiece 3. A coordinated process with each exhale is provided so that all expired air is captured, filtered, and sterilized before being vented into the environment behind the wearer. The two streams are kept separate to minimize the possibility of direct cross over. During respiratory pauses or apneic pauses (pauses between breaths whether metabolic or deliberate), the system 1 builds a curtain of sterilized air 10 to prevent ambient pathogens from drifting into the wearer's eyes, nose, or mouth.

Figure 9:
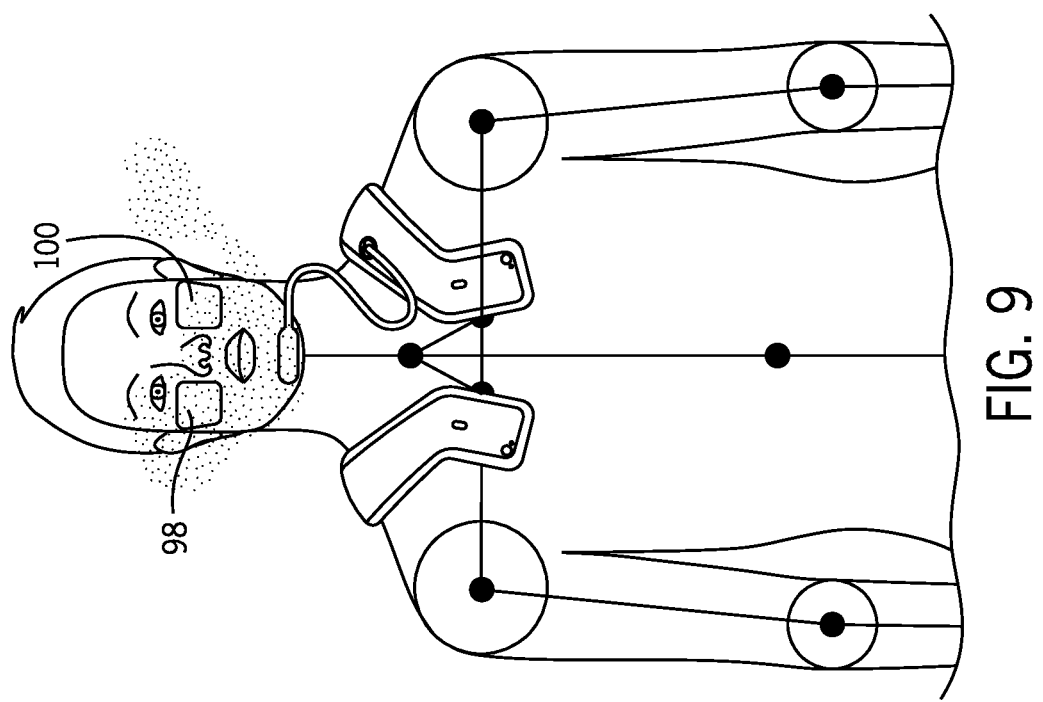
FIG. 9 illustrates the use of the exemplary wearable respiratory isolation system on a user, and, in particular, the operation of background oriented Schlieren imaging to determine whether the user is inhaling or exhaling.
Figure 10:
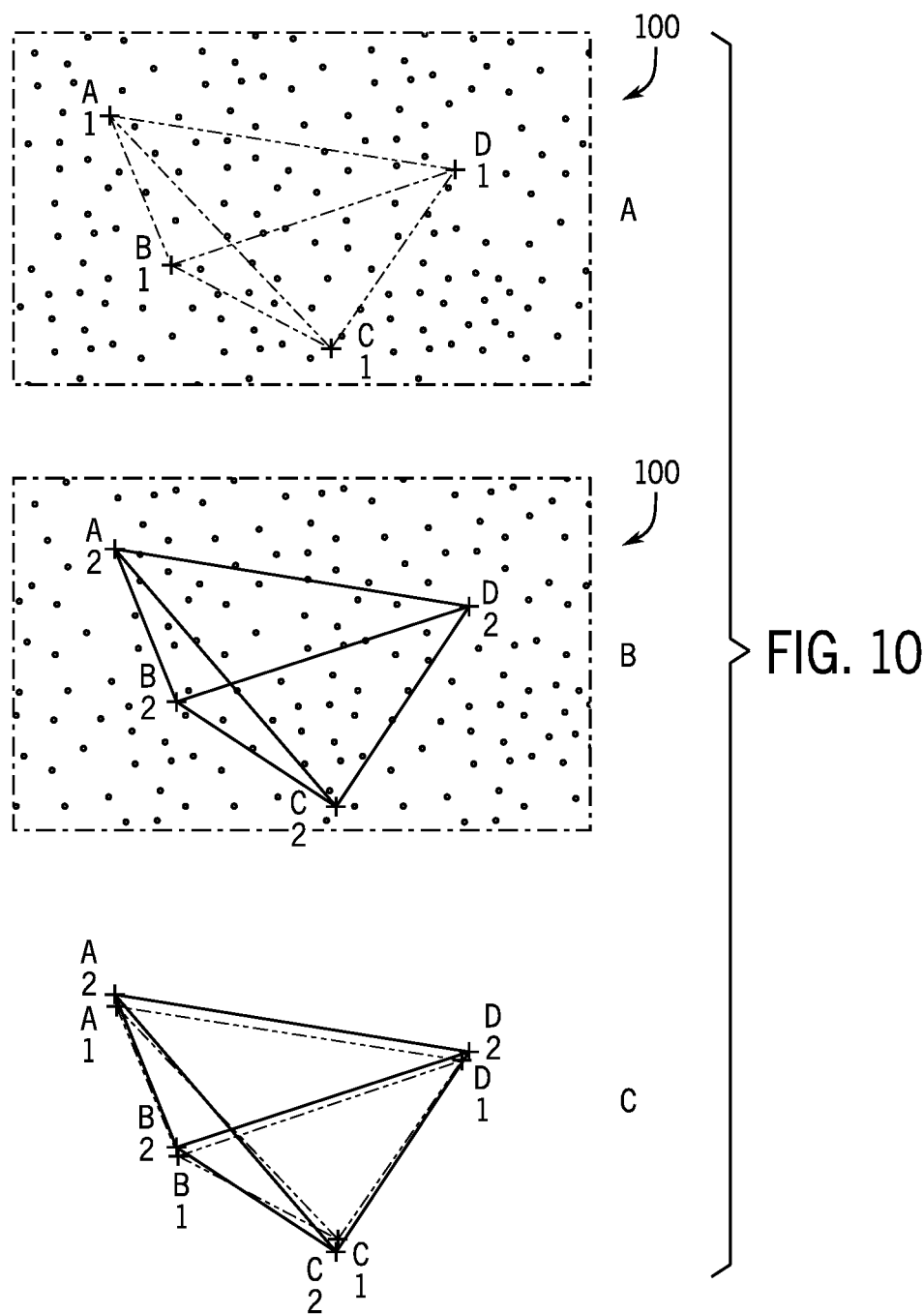
FIGS. 10A through 10C illustrate the use of a portion of a user's face as a background for background oriented Schlieren imaging FIG. 1

Through the use of sensing and computational approaches, the system 1 accounts for the amount of air inhaled on each breath, and ensures that a sufficient volume is provided to inhalation the entire inspiration, and that a sufficient volume is drawn in to capture the entire expiration. A group of individuals using this device in a closed environment, for example a teacher and her students, would be able to breathe, speak, and communicate freely while collectively reducing or eliminating ambient pathogens in their classroom. FIGS. 9 and 10 illustrate the use of modified, background oriented Schlieren (BOS) imaging in accordance with the exemplary embodiment of the invention. The exemplary system employs a modified, background oriented Schlieren (BOS) imaging technique to resolve the volume and direction of flow, based on time resolved changes in the localized refractive index. This modified version of (BOS), as mentioned above, is referred to in this document as Synthetic Adaptive Schlieren (SAS). The SAS technique involves the use of filtered high-resolution focal plane array imagers e.g., high speed cameras) to capture images of the ipsilateral maxillary region of the user's face and the contralateral maxillary region image of the user's face, with the contralateral path passing through the vestibular region and the ipsilateral path passing directly to the respective maxillary region. The illuminators illuminate the background patterns on the maxillary regions to simultaneously reference images and images from behind the flow target area in the vestibular region. Variations in refractive index cause the light from the background to differentially refract as it passes through the fluid, which causes a distortion of the pattern as resolved in the imager plane. Even though the change in refractive index is minute, the fineness of the pattern as well as the length of the off-axis optical path magnify this effect to the point that a shift is detectable. Image processing algorithms are used to quantify these effects and provide a quantitative vector image and data set. Integrating this image sequentially allows flow, magnitude, and direction to be resolved.

In the exemplary embodiment of the invention, the system employs a modified version of the technique described in the article entitled "Density measurements using near-field background-oriented Schlieren," by van Hinsburg and Rösgen, Exp Fluids (2014) 55:1720. The imagers 7 are filtered high-resolution focal plane array imagers (high-speed cameras), e.g., sample rate of 100 frame/sec, and the illuminators 7 are short wave, narrow band-UV (222 nm) LED's so that it is not noticeable to a person speaking to user and is safe to the user. Ambient light is filtered out so the imagers detect the wavelength (222 nm) emitted by the illuminators 7. In the modified technique and in accordance with the exemplary embodiment of the invention, the bioorganic surface of the wearer's face serves as the source of background information, see maxillary areas depicted by regions 98, 100 on the user's face in FIG. 9 above the alares and below the periorbita. These facial regions 98, 100 are rich in detail and do not shift rapidly. The maxillary regions 98, 100 are illuminated with a low level of the 222 nm light. The surface features most appropriate for this algorithm are facial pores situated in these areas, see FIGS. 10A through 10C. The patterns emergent from the area between the pores are used in the SAS imaging technique. FIG. 10A shows a set of identifiable data points A1, B1, C1, and D1 in a first image of facial region 100. FIG. 10B shows the set of identifiable data points in a second image of facial region 100. FIG. 10C shows the shift between the identifiable data points A1, B1, C1, and D1 and A2, B2, C2, and D2 caused by refraction. The image sampling rate is set at a rate so that motion of user is not significant to the calculations regarding refraction and airflow. Sequential imaging data is analyzed by software in real time to determine whether the image shows an inhaling air flow, an exhaling air flow, and if so the relative rate of air flow.

Synthetic Adaptive Schlieren (SAS)

Schlieren imaging has been used in the prior art to visualize and quantify flows of media, such as gases that are otherwise transparent, but have refractive index gradients due to local differences in temperature/pressure of the same fluid or variations of the concentration of components in mixtures and solutions. In the exemplary embodiment of the invention, these factors are detectable, and reflect differences between ambient air, inspired breaths, and expired breaths, regarding their temperature, pressure, and relative proportion of oxygen, carbon dioxide, and water vapor. Previous Schlieren data systems have been used in specific engineering problems such as heat transfer, leak detection, study of boundary layer detachment, and characterization of optics as well as gas anemometry. Previous applications often addressed phenomenon exhibiting far greater variability, making it considerably easier to detect changes in refractive indices, such as the study of shock waves in ballistics and the study of supersonic or hypersonic vehicles.

The use of a finely detailed background stochastic pattern to resolve optical ray shifts caused by refractive index perturbations is a principle previously used in background oriented Schlieren (BOS). Commonly, the stochastic pattern situated behind an area of interest is only resolvable in the far field using an optical system with an extended depth of field. The typical background oriented Schlieren technique relies on measuring or visualizing shifts in focused images. In these techniques, the background and the Schlieren object (the distortion to be visualized) are both in focus and the distortion is detected because part of the background image appears to have moved relative to its original position. Because of this focus requirement, they tend to be used for large-scale applications where both the Schlieren object and the background are distant (typically beyond the hyperfocal distance of the optical system). Since these systems require no additional optics aside from a camera, they are often the simplest to construct, though sensitivity is limited by the camera resolution. The technique also requires a suitable background image. In some cases, the background may be provided by the experimenter, such as a random speckle pattern or sharp line, though in some circumstances naturally occurring features such as landscapes or bright light sources such as the sun and moon can also be used.

Background oriented Schlieren is most often performed using software techniques such as digital image correlation and optical flow analysis to perform synthetic Schlieren. Normally, the only effect being tracked with Schlieren imaging is the instantaneous composite refractive index. It is necessary to integrate this repetitively in order to extract useable trend data. Static information gleaned from one frame lacks the temporal dimension by which vector flow may be adduced.

In optics, the refractive index (also known as refraction index or index of refraction) of a material is a dimensionless number that describes how fast light travels through the material. It is defined as: $n=c/v$, where c is the speed of light in vacuum and v is the phase velocity of light in the medium. For example, the refractive index (n) of water is 1.333, meaning that light travels 1.333 times as fast in vacuum as in water. Increasing refractive index corresponds to decreasing speed of light in the material.

The refractive index varies with wavelength, this causes white light to split into constituent colors when refracted. This is called dispersion. It can be observed in prisms and rainbows, and as chromatic aberration in lenses. Light propagation in absorbing materials can be described using a complex-valued refractive index. The imaginary part then handles the attenuation, while the real part accounts for refraction. For most materials, the refractive index changes with wavelength by several percent across the visible spectrum. Nevertheless, refractive indices for materials are commonly reported using a single value for n, typically measured at a specified wavelength both 589 nm (wavelength of sodium light) and 633 nm (HeNe laser) are common specifications.

Selected refractive indices at λ=589 nm.

| Material | n |
|---|---|
| Vacuum | 1 |
| Gases at 0° C. and 1 atm | |
| Air | 1.000293 |
| Helium | 1.000036 |
| Hydrogen | 1.000132 |
| Carbon dioxide | 1.00045 |
| Liquids at 20° C. | |
| Water | 1.333 |
| Ethanol | 1.36 |
| Olive oil | 1.47 |
| Solids | |
| Ice | 1.31 |
| Fused silica (quartz) | 1.46 |
| PMMA | 1.49 |
| Window glass | 1.52 |
| Polycarbonate (Lexan ™) | 1.58 |
| Flint glass (typical) | 1.69 |
| Sapphire | 1.77 |
| Cubic zirconia | 2.15 |
| Diamond | 2.42 |
| Moissanite | 2.65 |

To enhance the sensitivity of the BOS imaging system in the exemplary embodiment, narrow band, UVC 222 nm wavelength light is selected for imaging to increase discrimination between index changes. Since the direction of the illuminators 7 is towards the wearer in the exemplary embodiment of the invention, it is important that the illumination wavelength not be distracting or dangerous as mentioned previously, and the 222 nm wavelength satisfies this requirement. In addition, UVC light can be germicidal, further increasing its utility in this application.

Conventional germicidal UVC light (254 nm wavelength) is not desirable as this wavelength penetrates to some extent into the skin potentially posing a health hazard. In contrast, narrow band UVC light (222 nm wavelength) or far UVC radiation does not and is safe for the wearer. Far-UVC light penetrates less than 10 microns of this outer layer of the human skin or cornea, posing no threat to living cells. However, because bacteria and viruses are of micrometer or smaller dimensions, far-UVC can penetrate and inactivate them. Far-UVC has been shown to efficiently inactivate airborne aerosolized viruses, with a very low dose of 2 mW/cm$^2$ of 222-nm light, inactivating >95% of aerosolized H1N1 influenza virus. The suitability for Schlieren imaging, and the inactivation of pathogens, yet posing no risk of harm to the cornea or skin, combine to make the far UVC wavelength (222 nm) particularly well-suited for the invention. The refractive index at this wavelength (222 nm) in standard air: (15° C., 101.325 kPa and with 450 ppm CO2 content) is 1.00031132. As the wavelength is shortened, the refractive index increases logarithmically. The refractive index change due to gas density change may be quite small, therefore, enhancing the specific detectivity is necessary.

A modification of the constant correction factor in the known equations of the background-oriented Schlieren (BOS) is applicable to the near-field. Near-Field background-oriented Schlieren has the advantage over standard background-oriented Schlieren in being able to obtain reliable density distributions for set-ups in which the background pattern is placed directly behind the investigated flow field. The modified correction factor (this factor is part of the equations used for adjusting the shift of the ray passing through the flow field relative to the angular distortion of the far-field image) depends solely on the distance between the background pattern and the flow field, as well as the external shape of the probed flow.

Meier (1999) and Dalziel et al. (2000) introduced the background-oriented Schlieren (BOS) technique as a simplification of the traditional optical Schlieren system. BOS is based on recording background images using a camera. In order to determine the changes of the density variations within the volume, an additional undisturbed image has to be recorded as well. By applying a deconvolution process, a whole field projected deflection map is obtained in the viewing plane, showing not only the magnitude, but also the direction of the density gradients. This density gradient field is then integrated to obtain the projected density field.

The limitations of the BOS technique become apparent when applied to complex flow systems. The sensitivity of the BOS method depends, among other factors, on the apparent shift of the background pattern caused by the variations of the index of refraction along the line-of-sight. The apparent shift is a function of the density gradient, the distance between the investigated flow and the recoding medium and the distance between the investigated flow and the background pattern. For flow systems of which the latter distance is much smaller than the first, the measured apparent shift can become very small. This may lead to severe uncertainties in the calculated density fields.

Near-field background-oriented Schlieren (NF-BOS) is a method by which these difficulties can be overcome without sophisticated optical equipment. The NF-BOS method is sensitive to the first spatial derivative of the index of refraction, as long as these derivatives are perpendicular to the line-of-sight of the camera. The fluctuations in the light deflection through the investigated flow cause an apparent displacement of the background pattern in the horizontal and/or vertical directions.

To obtain this apparent shift, two images of the background pattern need to be recorded: a reference image without any deflection and a flow image with density variations. The apparent shift between the two images is calculated with a cross-correlation technique originally developed for PIV (particle image velocimetry). The in-plane shifts at the background plane is the actual width of the Schlieren object in the x and y in-plane coordinates, the undisturbed refractive index of the surrounding medium, refractive index of the intra flow, in addition to an overall correction factor for the near and far field.

This correction factor has been historically, and somewhat arbitrarily, set to a fixed integer value of 2. This value is only valid in the far-field. However, simulation of a synthetic Schlieren experiment demonstrated that this correction factor is in reality a variable parameter, not a fixed value.

However, merely using the NF variable correction factor is insufficient to expand the NF technique to situations where wide field ray tracing in the forefield is anticipated. It needs be adaptive based upon the distances as well as a temporally symmetrical pattern acquisition.

In order to overcome the distortion imposed upon a short forefield. Two synchronously acquired images of the same background from different perspective are digitally overlaid. One image is acquired through the field of interest and has the nearfield pattern as the background. The other image is acquired from a perspective that capture the same background but does not include the field of interest. These two images constitute chimeras of the same pattern and can therefore be co-registered through a correction algorithm. This approach generates a simultaneously acquired high accuracy reference image, with which to compare the apparent changes in the background induced by the media in the field of interest. Moreover, the technique is robust even if the background itself shifts—so long as movements are within a certain range of displacement and the changes are relatively slow compared to changes in the medium and rate of acquisition. Both of these conditions are met in the current application, wherein the background is a patch of facial skin overlying the maxilla captured from form ipsilateral and contralateral cameras on the embouchure. The skin overlying the maxilla exhibits relatively little movement. What little movement does occur is quite limited in the degree of distortion or displacement and is slow relative to the rate of data acquisition and the relevant changes in refractive index of inspired or expired breaths. This technique permits a short forefield to be used with a slowly distorting back pattern and is the principle underlying Synthetic Adaptive Schlieren (SAS) technique that is used in exemplary embodiment of the invention.

As implemented in the exemplary embodiment of the invention, Schlieren based detection provides real-time data as to inhalation, interphasal periods, exhalation and non-respiratory gas flow. As mentioned, on the embouchure 3 or mouthpiece 3 are two 222 nm directed incoherent illuminators. They are used to illuminate the transverse (relative to the handedness of the respective illuminator 6, 7) of the maxillary areas of the wearer. Also, as mentioned, coincident with each respective illuminator 6, 7 is a filtered high-resolution focal plane array sensor 6, 7 (e.g., specialized camera).

Images acquired by the cameras/sensors 6, 7 relate to the pattern created by the pore distribution on the maxillary areas 98, 100 of the wearer. They are corrected as to angular distortion and correlated into a synchronous reference image for concurrent image processing. The full maxillary background pattern is stitched together and is a stable interframe source for image processing.

The respiratory products by the wearer provide density contrast to precisely delineate the flow of exhalation products. However, the inspirational flow is only slightly perturbated by the low-pressure gradient provided by inspiration. Worse, the interphasal moment is even more difficult to detect. To overcome this limitation, the exemplary embodiment of the invention relies upon focused ultrasound as means to create a local modification of the density of the refracting medium.

A shaped ultrasonic transducer 9 is included on the embouchure 3. The ultrasonic transducer 11 projects a narrow cone of ultrasound into the areas of interest in the vestibular region of the mouth and nose. This ultrasound is modulated to be pulsed in a stepped fashion more than 5 times per second. This provides a rebounding density gradient that is predictable in its decay. The vital flow of this decaying medium is thereby directly imaged by the SAS imaging system. Movement of the flow is indicated with high accuracy by any unpredicted anomalous refractive index.

The SAS imaging system provides direct information about the vector flow at the vestibular area. This information is a vital component of the adaptive algorithm which both modulates the embouchure position as well as the supply and return modulation valves.

Rather, than developing images based upon a static reference background, SAS technique episodically collects the background image and carries the new image forward as an interframe reference source. A synthesized background image is available for reference allowing the emergent stochastic data set to be used in processing a series of subsequent images for relative flow resolution. The result is a data output indicating source, direction, and magnitude of flow.

Proper placement and orientation of the mouthpiece 3 or embouchure is important for the operational performance of the system 1. Optimal placement for the mouthpiece 3 is preferably determined by an adaptive algorithm, as mentioned. In the exemplary embodiment, the mouthpiece 3 position is fixed relative the user's face. Alternatively, the relative distance, position and attitude from the user's nostrils and mouth can also be adjusted for other factors including the speed and trajectory of air flow, and movement of the mouth apart from overall movement of the user's face. Feedback data may include acquisition of the stochastic background, movement of the mouth, and volume of respiratory exchange. These parameters are included in a feedback algorithm that dynamically readjusts the mouthpiece position several times a second. Heat and or moisture can be added to the inhalation gasses in order to facilitate detection of the sterilized air stream and consequently an inhaled breath. In addition, an ultrasonic horn (piezoelectric) can be mounted on the embouchure and directed at the user's face in order to provide a baseline disturbance to help improve the reliability of Schlieren detection.

Positioning and attitude adjustments of the mouthpiece 3 are made by the articulated arm 9, which comprises a four-segment umbilical in the exemplary embodiment. Referring again to FIGS. 1 through 4, to provide the necessary degree of dynamic positioning, each segment has two axes of freedom, which collectively allow flexion, extension, and movement in any direction within the range of arm 9. The mouthpiece 3 or embouchure lies at the distal end of the articulating arm 9. The proximal attachment of the articulating arm 9 includes a powered control mechanism 102 that drives friction sprockets to pull on cables to manipulate the positioning of the umbilical sections, similar to the technology used for endoscopes. The drive in the exemplary embodiment uses piezoelectric motors to drive the respective friction sprockets. An air inhalation conduit (not shown) and an exhaust gas conduit (not shown) are located within the articulated arm 9. The proximal end of the articulated arm 9 includes a magnetic plug 102 for attachment to the collar 2. The magnetic plug 102 provides connections 82, 84 for the air inhalation and exhaust gas conduits. The plug 102 also provides electrical connections for DC power, data signals and control signals for the control mechanism 102 of the articulated arm 9, the modulation valves 16, 17, the imagers/illuminators 6, 7, ultrasonic transducer 11 and microphone 8 on the multipiece 3. At the point of attachment, the integrated control mechanism 102 is driven by control electronics whose input is based upon data derived from imaging sensors in the mouthpiece 3. As previously discussed, in operation, the articulating arm 9 actively tracks the wearer's movements and adjusts instantly, maintaining optimal positioning of the mouthpiece/embouchure 3 relative to the nose and mouth to precisely deliver sterilized air and capture exhaled respirations.

Paroxysmal or episodic events such as sneezing, and coughing are distinct from normal breathing and are addressed differently from normal respiration in the exemplary embodiment. A typical cough has three phases beginning with a deep inspiratory phase characterized by an enhanced contraction of the diaphragm and opening of the vocal cords (glottis), by the abductor muscles of the larynx. This is followed by a compressive phase characterized by closure of the glottis and contraction of the expiratory muscles. After a short pause during which pressure builds, an expulsive phase commences—resulting from a spasmodic opening of the glottis coupled with continued forceful contraction of the expiratory muscles.

A sneeze is similar, though there may be multiple inspirations, without an intervening exhalation—the Ah, Ah, Ah—portion of the sneeze leading to large lung volumes, a similar compressive phase with closure of the glottis and contraction of the expiratory muscles, and an expulsive phase with sudden opening of the glottis coupled with continued forceful contraction of the expiratory muscles. Though in this case the tongue and palate allow air to be expelled through the naso-pharynx and out the nose.

These unique characteristics, namely the sudden deep inspiration and subsequent pause associated with the inspiratory and compressive phase, are detected by system and are preferably used to pre-emptively mitigate the effects, using a predictive algorithm. The volume and contents of one or a series of coughs should be able to be captured by the system by rapidly emptying the exhaust reservoir and temporarily increasing the rate and volume of the exhaust flow. Unlike coughing, sneezing generates a variety of ejects, and its full capture during the exhaust cycle is unlikely.

In the exemplary embodiment of the invention, the system 1 upon detection of an incipient sneeze (or a cough or other event that is beyond the normal capability of the exhaust system) provides an upward burst of sterilized air from the inhalation reservoir 38. This jet deflects the paroxysmal stream up and away from the faces of nearby individuals, thereby minimizing direct exposure. In addition, as mentioned, the system contains several small canisters of amendments that can be dosed into the inhalation reservoir 38 and possibly used to mitigate paroxysmal events such as sneezing.

Alternatively, the system 1 can be programmed to acknowledge that the user is expected to cover their nose and mouth with a handkerchief or elbow in the event of a sneeze or cough. In this alternative mode of operation, the system 1 enters a collection mode in which it does provide sterilized air but activates the exhaust fans at a high level until the paroxysmal event is resolved and user returns to a normal respiratory pattern.

Alternative methods of sensing respiration can include measuring: blood oximetry; air pressure; air flow; microphonics; chest or diaphragm movements via strain, pressure, acceleration, resistance, voltage, capacitance, etc. The sensor could contain a combination of a plurality of these methods. These embodiments are less desirable than the exemplary one described herein. The invention disclosed is not limited by the sensing method.

Breathe-through masks fare badly and should be changed after such paroxysmal events. This is a requirement familiar to medical professionals, however, casual users typically sneeze into the mask and fail to dispose of the contaminated mask. Continued use of a contaminated mask produces a contaminated plume which is counterproductive. Unlike masks, the wearable respiratory isolation system 1 describe herein does not require replacement in the event of a sneeze. Cleaning with a wipe would suffice to return asepsis.

Referring to again to FIGS. 3 and 4, as mentioned, the canisters 72, 74, 76 or the ability to use canisters is an optional feature. FIG. 4 shows an extension 104 containing canisters 72, 74, 76. The extension 104 can be magnetically attached to the back of the collar 2, see FIG. 3. The extension 104 includes flow channels for the intake air and the exhaust air thereby positioning the exhaust outlet 80 farther away from the user's face than when the extension 104 is not used.

The neck portion of the collar 2 is desirably bendable so that the collar 2 can be fitted comfortably over the shoulders and neck of the user.

It is desired that the system 1 be largely or completely waterproof, and easy to clean. FIG. 2 shows filter inserts which include a holder 106, 108 for the respective MERV filter 88, 50. The holders 106, 108 are sealed and reusable, whereas the filers 50, 88 are disposable. Further, as previously discussed, many of the components in the system are constructed as part of removable modules. This modular construction facilitates the ability to clean and maintain the unit with ease.

The invention has been described above primarily with respect to an exemplary embodiment of the invention. Certain innovative aspects of the invention may and are likely to be useful in connections with other embodiments that do not include other aspects of the invention described in connection with the exemplary embodiment depicted in the drawings. For example, as mentioned previously while it is preferred to use a modified, background oriented Schlieren imaging technology, many aspects of the invention can be used with other sensors or methods for detecting the breathing pattern of the wearer. Also, the manner of sterilization of the inhalation air and or the exhaust air can be modified within the scope of the invention. Similarly, while the open collar 2 embodiment is deemed desirable, the components of the wearable can take other forms such a vest, hat, visor or belt.

What is claimed is:

1. A wearable respiratory isolation system comprising:
    an air inhalation path configured to intake air through an intake vent and to supply a filtered and sterilized air stream from an inhalation vent adapted to be located near the face of a user, wherein the inhalation vent is configured so that a cloud of filtered and sterilized air is presented in front of a nose and mouth of the user when the user inhales;
    intake filtering and sterilizing means for filtering and sterilizing the air passing through the inhalation path;
    a first air moving means for moving air through the inhalation path such that air passes through said intake filtering and sterilizing means at a sufficient rate to adequately filter and sterilize air passing through the inhalation path;
    a sterilized inhalation reservoir located in the inhalation path downstream of said intake filtering and sterilizing means;
    an inhalation valve configured to control the flow of the filtered and sterilized gasses from the sterilized inhalation reservoir through the inhalation vent, said air inhalation valve being normally closed when the user is exhaling;
    an exhalation air path configured to intake air through an exhalation vent adapted to be located near the face of the user and to output decontaminated air from an exhaust outlet vent adapted to be located away from the face of the user;
    exhaust decontamination means for decontaminating the air passing through the exhalation air path;
    a second air moving means for drawing air and gasses into the exhalation vent located near the face of the user and through the exhalation path at a sufficient rate to capture gasses expired by the user in combination with ambient air in order that essentially all expired gasses are entrained within the air flow through the exhalation path;

an exhalation valve configured to control the flow of air into the exhalation vent;

a sensor configured to output data representing whether the user is inhaling, exhaling or is neither inhaling nor exhaling; and a controller configured to control operation of the air inhalation valve and the exhalation valve in response to the data;

wherein the inhalation vent and the exhalation vent are both located on an embouchure that is connected to an articulated arm, wherein the controller is further configured to control the articulated arm to track movement of the user in order to place the air inhalation vent and the exhalation vent in front of the mouth and nostrils of the user.

2. The wearable respiratory isolation system according to claim 1 wherein the sensor comprises an ipsilateral imager, an ipsilateral illuminator, a contralateral imager, a contralateral illuminator and software configured to implement a background oriented Schlieren imaging algorithm in real time to determine whether the user is inhaling or exhaling and if so configured to determine the level of inhalation or exhalation; and further wherein the imagers, the illuminators, the inhalation vent and the exhalation vent are each located on the embouchure that is connected to the articulated arm; the background used for said background oriented Schlieren imaging comprises maxillary regions of the face of the user; and the imagers are configured to sense movement of the face of the user in order to place the embouchure in front of the mouth and nostrils of the user and in a desired location relative to the mouth and nostrils of the user.

3. The wearable respiratory isolation system recited in claim 1 wherein said intake filtering and sterilizing means comprises a particulate ionization precipitator within an LED UV-C germicide chamber and a filter located upstream of the LED UV-C germicide chamber.

4. The wearable respiratory isolation system recited in claim 1 wherein said exhaust decontamination means comprises a particulate ionization precipitator within an LED UV-C germicide chamber and a filter located upstream of the LED UV-C germicide chamber.

5. The wearable respiratory isolation system recited in claim 1 wherein the controller is configured to control the articulated arm to track the movement of the user by sensing one or both areas on the face of the user above the alares and below the periorbita.

6. The wearable respiratory isolation system recited in claim 1 further comprising an oxygen sensor to sense the oxygen content of the filtered and sterilized air supplied through the air inhalation vent.

7. The wearable respiratory isolation system recited in claim 1 wherein the controller is configured to control operation of the air inhalation valve, based on the data from the sensor, to release at least a low level of air flow at all times during a normal respiration cycle when the user is not exhaling, to be closed when the user is exhaling and further to release higher levels of air flow beyond said low level of air flow when the user is inhaling.

8. The wearable respiratory isolation system recited in claim 2 further comprising a piezoelectric, ultrasonic horn located on the embouchure and configured to be directed towards the face of the user, wherein said imagers and software are configured to detect ultrasonic waves to supplement the resolution of the background oriented Schlieren imaging algorithm.

9. The wearable respiratory isolation system recited in claim 1 wherein the articulated arm comprises multiple umbilical segments to manipulate the positioning of a distal end of the articulating arm and the embouchure and the system further comprises piezoelectric friction motors for moving the articulated arm.

10. The wearable respiratory isolation system recited in claim 2 wherein the illuminators are configured to output invisible light within a narrow wavelength band of about 222 nm, and the imagers include filters to block ambient light but allow light in the narrow wavelength band of about 222 nm to pass to the respective imager.

\* \* \* \* \*